US010358671B2

(12) United States Patent
Kawakami et al.

(10) Patent No.: US 10,358,671 B2
(45) **Date of Patent: *Jul. 23, 2019**

(54) PROTEIN PRODUCTION METHOD

(71) Applicants: KYOWA HAKKO KIRIN CO., LTD, Tokyo (JP); Inter-University Research Institute Corporation Research Organization of Information and Systems, Tachikawa-shi, Tokyo (JP)

(72) Inventors: Koichi Kawakami, Mishima (JP); Keina Yamaguchi, Takasaki (JP); Risa Ogawa, Takasaki (JP); Masayoshi Tsukahara, Takasaki (JP)

(73) Assignees: KYOWA HAKKO KIRIN CO., LTD, Tokyo (JP); Inter-University Research Institute Corporation Research Organization of Information and Systems, Tokyo (JP)

( * ) Notice: Subject to any disclaimer, the term of this patent is extended or adjusted under 35 U.S.C. 154(b) by 188 days.

This patent is subject to a terminal disclaimer.

(21) Appl. No.: 15/639,571

(22) Filed: Jun. 30, 2017

(65) Prior Publication Data

US 2017/0306378 A1 Oct. 26, 2017

Related U.S. Application Data

(63) Continuation of application No. 14/689,782, filed on Apr. 17, 2015, now Pat. No. 9,725,750, which is a continuation of application No. 12/813,920, filed on Jun. 11, 2010, now Pat. No. 9,034,649.

(60) Provisional application No. 61/186,138, filed on Jun. 11, 2009.

(30) Foreign Application Priority Data

Jun. 11, 2009 (JP) ................................ 2009-140626

(51) Int. Cl.

| | |
|---|---|
| ***C12P 21/00*** | (2006.01) |
| ***C07K 16/10*** | (2006.01) |
| ***C12P 21/02*** | (2006.01) |
| ***C12N 15/85*** | (2006.01) |

(52) U.S. Cl.

CPC .......... *C12P 21/00* (2013.01); *C07K 16/1018* (2013.01); *C12N 15/85* (2013.01); *C12P 21/02* (2013.01); *C12N 2015/8518* (2013.01); *C12N 2800/107* (2013.01); *C12N 2800/90* (2013.01); *C12N 2840/20* (2013.01)

(58) Field of Classification Search

None

See application file for complete search history.

(56) References Cited

U.S. PATENT DOCUMENTS

| | | | |
|---|---|---|---|
| 6,291,243 | B1 | 9/2001 | Fogarty et al. |
| 6,475,798 | B2 | 11/2002 | Fogarty et al. |
| 7,064,194 | B2 | 6/2006 | Misawa et al. |
| 7,195,915 | B2 | 3/2007 | Misawa et al. |
| 7,737,325 | B2 | 6/2010 | Kanda et al. |
| 2002/0028513 | A1 | 3/2002 | Fogarty et al. |
| 2003/0037346 | A1 | 2/2003 | Craig et al. |
| 2004/0029229 | A1 | 2/2004 | Reeves et al. |
| 2004/0242512 | A1 | 12/2004 | Misawa et al. |
| 2005/0177890 | A1 | 8/2005 | Kawakami |
| 2006/0078992 | A1 | 4/2006 | Misawa et al. |
| 2006/0141627 | A1 | 6/2006 | Comer |
| 2010/0129914 | A1 | 5/2010 | Koga et al. |
| 2010/0311116 | A1 | 12/2010 | Wurm et al. |

FOREIGN PATENT DOCUMENTS

| | | |
|---|---|---|
| JP | 2003235575 | 8/2003 |
| WO | 0065042 | 11/2000 |
| WO | 0194571 | 12/2001 |
| WO | 02072843 | 9/2002 |
| WO | 2004016792 | 2/2004 |
| WO | 2007082164 | 7/2007 |
| WO | 2008072540 | 6/2008 |
| WO | 2008100424 | 8/2008 |
| WO | 2009046978 | 4/2009 |
| WO | 2009071334 | 6/2009 |

OTHER PUBLICATIONS

Amendment Under 37 C.F.R. § 1.111, submitted to U.S. Patent and Trademark Office dated Jan. 9, 2014 in response to Non-Final Office Action dated Sep. 9, 2013.

Response to Restriction Requirement, submitted to the U.S. Patent and Trademark Office dated Jun. 28, 2013 in response to Restriction Requirement dated May 30, 2013.

(Continued)

*Primary Examiner* — Suzanne M Noakes

*Assistant Examiner* — Jae W Lee

(74) *Attorney, Agent, or Firm* — Sughrue Mion, PLLC

(57) ABSTRACT

This invention relates to a method for producing a protein of interest, comprising introducing a protein expression vector which comprises a gene fragment a gene fragment comprising a DNA encoding a protein of interest and a selectable marker gene and transposon sequences at both terminals of the gene fragment, into a suspension mammalian cell; integrating the gene fragment inserted between a pair of the transposon sequences, into a chromosome of the mammalian cell to obtain a mammalian cell capable of expressing the protein of interest; and suspension-culturing the mammalian cell; and a suspension mammalian cell capable of expressing the protein of interest.

16 Claims, 7 Drawing Sheets

Specification includes a Sequence Listing.

(56) References Cited

OTHER PUBLICATIONS

Balciunas et. al. "Harnessing a High Cargo-Capacity Transposon for Genetic Applications in Vertebrates", PLOS Genetics, 2(11):1715-1724 (2006).
Cadinanos et. al. "Generation of an inducible and optimized piggyBac transposon system", Nucleic Acids Research, 35(12):1-8 (2007).
Huang et al., "Gene Transfer Efficiency and Genome-Wide Integration Profiling of Sleeping Beauty, Tol2, and PiggyBac Transposons in Human Primary T Cells", The American Society of Gene & Cell Therapy, 18(10):1803-1813 (2010).
Ivics et. al. "Molecular Reconstruction of sleeping Beauty, a Tc1-like Transposon from Fish, and Its Transposition in Human Cells", Cell, 91:501-510 (1997).
Kawakami, "Tol2: a versatile gene transfer vector in vertebrates", Genome Biology, 8(Suppl 1):S7.1-S7.10 (2007).
Kawakami et. al., "Transposition of the Tol2 Element, an Ac-Like Element From the Japanese Medaka Fish *Oryzias latipes* in Mouse Embryonic Stem Cells", Genetics Society of America, 166:895-899 (2004).
Kodama et. al., "The Tol1 element of the medaka fish, a member of the hAT transposable element family, jumps in Caenorhabditis elegans", Heredity, 101:222-227 (2008).
Koga et. al., "Germline Transgenesis of Zebrafish Using the Medaka Tol1 Transposon System", Development Dynamics, 237:2466-2474 (2008).
Koga et. al., "The Tol1 element of medaka fish is transposed with only terminal regions and can deliver large DNA fragments into the chromosomes", Journal of Human Genetics, 52:1026-1030 (2007).
Koga et. al., "The Tol1 transposable element of the medaka fish moves in human and mouse cells", Journal of Human Genetics, 52:628-635 (2007).
Koga et. al., "Transposable element in fish", Nature, 383:30 (1996).
Koo et. al., "Beneficial effect of 30Kc6 gene expression on production of recombinant interferon-B in serum-free suspension culture of CHO cells", Process Biochemistry, 44:146-153 (2009).
Kwan et al., "The Tol2kit: A Multisite Gateway-Based Construction Kit for Tol2 Transposon Transgenesis Constructs", Developmental Dynamics, pp. 3088-3099 (2007).
Lattenmayer et al., "Protein-Free Transfection of CHO Host Cells With an IgG-Fusion Protein: Selection and Characterization of Stable High Producers and Comparison to Conventionally Transfected Clones", Biotechnology and Bioengineering, 96(6):1118-1126 (2007).
Luo et. al., "Chromosomal transposition of a Tc1/mariner-like element in mouse embryonic stem cells", The National Academy of Sciences, 95:10769-10773 (2008).
Miskey et. al., "The Frog Prince: a reconstructed transposon from Rana pipiens with high transpositional activity in vertebrate cells", Nucleic Acids Research, 31(23):6873-6881 (2003).
Office Action for Taiwanese Application No. 099119233 dated Sep. 26, 2014.
Office Action for Chinese Patent Application No. 201080026008.5 dated Mar. 14, 2014.
Office Action for Chinese Application No. 201080026008.5 dated May 2, 2013.
Office Action for U.S. Appl. No. 13/326,873 dated Sep. 9, 2013.
Communication for European Patent Application 10786229.4 dated Dec. 6, 2013.
PCT/ISA/210 for Japanese Patent Application No. PCT/JP2010/059881 issued Jul. 13, 2010.
PCT/ISA/237 for Japanese Patent Application No. PCT/JP2010/059881 issued Jul. 13, 2010.
Poche et al. "Resistance against Cycloheximide in Cell Lines from Chinese Hamster and Human Cells is Conferred by the Large Subunit of Cytoplasmic Ribosomes", Molec. Gen. Genet., 175:181-185 (1979).
Schifferli et. al., "Transfection of Suspension Cultures of CHO Cells", Focus, 21(1):16-17 (1999).
Communication for U.S. Appl. No. 13/326,873 dated Sep. 9, 2013.
Communication for U.S. Appl. No. 13/326,873 dated May 30, 2013.
Communication for European Patent Application No. 10786229.4 dated Dec. 6, 2013.
Urasaki et. al. "Functional Dissection of the Tol2 Transposable Element Identified the Minimal cis-Sequence and a Highly Repetitive Sequence in the Subterminal Region Essential for Transposition", Genetics Society of America, 174:639-649 (2006).
Wu et. al., "piggyBac is a flexible and highly active transposon as compared to Sleeping Beauty, Tol2, and Mos1 in mammalian cells", PNAS, 103(41):15008-15013 (2006).
Dupuy et. al., "Mammalian mutagenesis using a highly mobile somatic Sleeping Beauty transposon system", Nature, 436:221-226 (2005).
Fischer et. al., "Regulated transposition of a fish transposon in the mouse germ line", PNAS, 98(12):6759-6764 (2001).
Fraser et. al., "Precise excision of TTAA-specific lepidopteran transposons piggyBac (IFP2) and tagalong (TFP3) from the baculovirus genome in cell lines two species of *Lepidoptera*", Insect Molecular Biology, 5(2):141-151 (1998).

SEQUENCE LISTING

```
<160> NUMBER OF SEQ ID NOS: 17

<210> SEQ ID NO 1
<211> LENGTH: 2788
<212> TYPE: DNA
<213> ORGANISM: Artificial
<220> FEATURE:
<223> OTHER INFORMATION: Synthetic construct of nonautologus Tol2
      transposon

<400> SEQUENCE: 1

cagaggtgta aagtacttga gtaattttac ttgattactg tacttaagta ttatttttgg      60

ggatttttac tttacttgag tacaattaaa aatcaatact tttactttta cttaattaca     120

ttttttttaga aaaaaaagta ctttttactc cttacaattt tatttacagt caaaaagtac     180

ttattttttg gagatcactt cattctattt tcccttgcta ttaccaaacc aattgaattg     240

cgctgatgcc cagtttaatt taaatgttat ttattctgcc tatgaaaatc gttttcacat     300

tatatgaaat tggtcagaca tgttcattgg tcctttggaa gtgacgtcat gtcacatcta     360

ttaccacaat gcacagcacc ttgacctgga aattagggaa attataacag tcaatcagtg     420
```

```
gaagaaaatg gaggaagtat gtgattcatc agcagctgcg agcagcacag tccaaaatca    480
gccacaggat caagagcacc cgtggccgta tcttcgcgaa ttctttttctt taagtggtgt    540
aaataaagat tcattcaaga tgaaatgtgt cctctgtctc ccgcttaata aagaaatatc    600
ggccttcaaa agttcgccat caaacctaag gaagcatatt gaggtaagta cattaagtat    660
tttgttttac tgatagtttt tttttttttt tttttttttt tttttgggtg tgcatgtttt    720
gacgttgatg gcgcgccttt tatatgtgta gtaggcctat tttcactaat gcatgcgatt    780
gacaatataa ggctcacgta ataaaatgct aaaatgcatt tgtaattggt aacgttaggt    840
ccacgggaaa tttggcgcct attgcagctt tgaataatca ttatcattcc gtgctctcat    900
tgtgtttgaa ttcatgcaaa acacaagaaa accaagcgag aaattttttt ccaaacatgt    960
tgtattgtca aaacggtaac actttacaat gaggttgatt agttcatgta ttaactaaca   1020
ttaaataacc atgagcaata catttgttac tgtatctgtt aatctttgtt aacgttagtt   1080
aatagaaata cagatgttca ttgtttgttc atgttagttc acagtgcatt aactaatgtt   1140
aacaagatat aaagtattag taaatgttga aattaacatg tatacgtgca gttcattatt   1200
agttcatgtt aactaatgta gttaactaac gaaccttatt gtaaaagtgt taccatcaaa   1260
actaatgtaa tgaaatcaat tcaccctgtc atgtcagcct tacagtcctg tgtttttgtc   1320
aatataatca gaaataaaat taatgtttga ttgtcactaa atgctactgt atttctaaaa   1380
tcaacaagta tttaacatta taaagtgtgc aattggctgc aaatgtcagt tttattaaag   1440
ggttagttca cccaaaaatg aaaataatgt cattaatgac tcgccctcat gtcgttccaa   1500
gcccgtaaga cctccgttca tcttcagaac acagtttaag atattttaga tttagtccga   1560
gagctttctg tgcctccatt gagaatgtat gtacggtata ctgtccatgt ccagaaaggt   1620
aataaaaaca tcaaagtagt ccatgtgaca tcagtgggtt agttagaatt ttttgaagca   1680
tcgaatacat tttggtccaa aaataacaaa acctacgact ttattcggca ttgtattctc   1740
ttccgggtct gttgtcaatc cgcgttcacg acttcgcagt gacgctacaa tgctgaataa   1800
agtcgtaggt tttgttattt ttggaccaaa atgtattttc gatgcttcaa ataattctac   1860
ctaacccact gatgtcacat ggactacttt gatgttttta ttacctttct ggacatggac   1920
agtataccgt acatacattt tcagtggagg gacagaaagc tctcggacta aatctaaaat   1980
atcttaaact gtgttccgaa gatgaacgga ggtgttacgg gcttggaacg acatgagggt   2040
gagtcattaa tgacatcttt tcatttttgg gtgaactaac cctttaatgc tgtaatcaga   2100
gagtgtatgt gtaattgtta catttattgc atacaatata aatatttatt tgttgttttt   2160
acagagaatg cacccaaatt acctcaaaaa ctactctaaa ttgacagcac agaagagaaa   2220
gatcgggaca gatctcatat gctcgagggc ccatctggcc tgtgtttcag acaccaggga   2280
gtctctgctc acgtttcctg ctatttgcag cctctctatc aagactaata cacctcttcc   2340
cgcatcggct gcctgtgaga ggcttttcag cactgcagga ttgcttttca gccccaaaag   2400
agctaggctt gacactaaca attttgagaa tcagcttcta ctgaagttaa atctgaggtt   2460
ttacaacttt gagtagcgtg tactggcatt agattgtctg tcttatagtt tgataattaa   2520
atacaaacag ttctaaagca ggataaaacc ttgtatgcat ttcatttaat gttttttgag   2580
attaaaagct taaacaagaa tctctagttt tctttcttgc ttttactttt acttccttaa   2640
tactcaagta caattttaat ggagtacttt tttactttta ctcaagtaag attctagcca   2700
gatactttta cttttaattg agtaaaattt tccctaagta cttgtacttt cacttgagta   2760
aaatttttga gtacttttta cacctctg                                      2788
```

<210> SEQ ID NO 2
<211> LENGTH: 200
<212> TYPE: DNA
<213> ORGANISM: Artificial
<220> FEATURE:
<223> OTHER INFORMATION: Synthetic construct of Tol2-L transposon sequence

<400> SEQUENCE: 2

```
cagaggtgta aagtacttga gtaattttac ttgattactg tacttaagta ttatttttgg     60

ggatttttac tttacttgag tacaattaaa aatcaatact tttactttta cttaattaca    120

ttttttaga aaaaaaagta ctttttactc cttacaattt tatttacagt caaaaagtac    180

ttattttttg gagatcactt                                                200
```

<210> SEQ ID NO 3
<211> LENGTH: 504
<212> TYPE: DNA
<213> ORGANISM: Artificial
<220> FEATURE:
<223> OTHER INFORMATION: Synthetic construct of Tol2-R transposon sequence

<400> SEQUENCE: 3

```
ctgctcacgt ttcctgctat ttgcagcctc tctatcaaga ctaatacacc tcttcccgca     60

tcggctgcct gtgagaggct tttcagcact gcaggattgc ttttcagccc caaaagagct    120

aggcttgaca ctaacaattt tgagaatcag cttctactga agttaaatct gaggttttac    180

aactttgagt agcgtgtact ggcattagat tgtctgtctt atagtttgat aattaaatac    240

aaacagttct aaagcaggat aaaaccttgt atgcatttca tttaatgttt tttgagatta    300

aaagcttaaa caagaatctc tagttttctt tcttgctttt acttttactt ccttaatact    360

caagtacaat tttaatggag tacttttttta cttttactca agtaagattc tagccagata    420

cttttacttt taattgagta aaattttccc taagtacttg tactttcact tgagtaaaat    480

ttttgagtac tttttacacc tctg                                           504
```

<210> SEQ ID NO 4
<211> LENGTH: 2156
<212> TYPE: DNA
<213> ORGANISM: Oryzias latipes
<220> FEATURE:
<221> NAME/KEY: CDS
<222> LOCATION: (85)..(2034)

<400> SEQUENCE: 4

```
acgtcatgtc acatctatta ccacaatgca cagcaccttg acctggaaat tagggaaatt     60

ataacagtca atcagtggaa gaaa atg gag gaa gta tgt gat tca tca gca      111
                           Met Glu Glu Val Cys Asp Ser Ser Ala
                           1               5

gct gcg agc agc aca gtc caa aat cag cca cag gat caa gag cac ccg      159
Ala Ala Ser Ser Thr Val Gln Asn Gln Pro Gln Asp Gln Glu His Pro
10                  15                  20                  25

tgg ccg tat ctt cgc gaa ttc ttt tct tta agt ggt gta aat aaa gat      207
Trp Pro Tyr Leu Arg Glu Phe Phe Ser Leu Ser Gly Val Asn Lys Asp
                30                  35                  40

tca ttc aag atg aaa tgt gtc ctc tgt ctc ccg ctt aat aaa gaa ata      255
Ser Phe Lys Met Lys Cys Val Leu Cys Leu Pro Leu Asn Lys Glu Ile
            45                  50                  55

tcg gcc ttc aaa agt tcg cca tca aac cta agg aag cat att gag aga      303
```

```
Ser Ala Phe Lys Ser Ser Pro Ser Asn Leu Arg Lys His Ile Glu Arg
        60                  65                  70

atg cac cca aat tac ctc aaa aac tac tct aaa ttg aca gca cag aag      351
Met His Pro Asn Tyr Leu Lys Asn Tyr Ser Lys Leu Thr Ala Gln Lys
    75                  80                  85

aga aag atc ggg acc tcc acc cat gct tcc agc agt aag caa ctg aaa      399
Arg Lys Ile Gly Thr Ser Thr His Ala Ser Ser Ser Lys Gln Leu Lys
90                  95                  100                 105

gtt gac tca gtt ttc cca gtc aaa cat gtg tct cca gtc act gtg aac      447
Val Asp Ser Val Phe Pro Val Lys His Val Ser Pro Val Thr Val Asn
                110                 115                 120

aaa gct ata tta agg tac atc att caa gga ctt cat cct ttc agc act      495
Lys Ala Ile Leu Arg Tyr Ile Ile Gln Gly Leu His Pro Phe Ser Thr
            125                 130                 135

gtt gat ctg cca tca ttt aaa gag ctg att agt aca ctg cag cct ggc      543
Val Asp Leu Pro Ser Phe Lys Glu Leu Ile Ser Thr Leu Gln Pro Gly
        140                 145                 150

att tct gtc att aca agg cct act tta cgc tcc aag ata gct gaa gct      591
Ile Ser Val Ile Thr Arg Pro Thr Leu Arg Ser Lys Ile Ala Glu Ala
    155                 160                 165

gct ctg atc atg aaa cag aaa gtg act gct gcc atg agt gaa gtt gaa      639
Ala Leu Ile Met Lys Gln Lys Val Thr Ala Ala Met Ser Glu Val Glu
170                 175                 180                 185

tgg att gca acc aca acg gat tgt tgg act gca cgt aga aag tca ttc      687
Trp Ile Ala Thr Thr Thr Asp Cys Trp Thr Ala Arg Arg Lys Ser Phe
                190                 195                 200

att ggt gta act gct cac tgg atc aac cct gga agt ctt gaa aga cat      735
Ile Gly Val Thr Ala His Trp Ile Asn Pro Gly Ser Leu Glu Arg His
            205                 210                 215

tcc gct gca ctt gcc tgc aaa aga tta atg ggc tct cat act ttt gag      783
Ser Ala Ala Leu Ala Cys Lys Arg Leu Met Gly Ser His Thr Phe Glu
        220                 225                 230

gta ctg gcc agt gcc atg aat gat atc cac tca gag tat gaa ata cgt      831
Val Leu Ala Ser Ala Met Asn Asp Ile His Ser Glu Tyr Glu Ile Arg
    235                 240                 245

gac aag gtt gtt tgc aca acc aca gac agt ggt tcc aac ttt atg aag      879
Asp Lys Val Val Cys Thr Thr Thr Asp Ser Gly Ser Asn Phe Met Lys
250                 255                 260                 265

gct ttc aga gtt ttt ggt gtg gaa aac aat gat atc gag act gag gca      927
Ala Phe Arg Val Phe Gly Val Glu Asn Asn Asp Ile Glu Thr Glu Ala
                270                 275                 280

aga agg tgt gaa agt gat gac act gat tct gaa ggc tgt ggt gag gga      975
Arg Arg Cys Glu Ser Asp Asp Thr Asp Ser Glu Gly Cys Gly Glu Gly
            285                 290                 295

agt gat ggt gtg gaa ttc caa gat gcc tca cga gtc ctg gac caa gac     1023
Ser Asp Gly Val Glu Phe Gln Asp Ala Ser Arg Val Leu Asp Gln Asp
        300                 305                 310

gat ggc ttc gaa ttc cag cta cca aaa cat caa aag tgt gcc tgt cac     1071
Asp Gly Phe Glu Phe Gln Leu Pro Lys His Gln Lys Cys Ala Cys His
    315                 320                 325

tta ctt aac cta gtc tca agc gtt gat gcc caa aaa gct ctc tca aat     1119
Leu Leu Asn Leu Val Ser Ser Val Asp Ala Gln Lys Ala Leu Ser Asn
330                 335                 340                 345

gaa cac tac aag aaa ctc tac aga tct gtc ttt ggc aaa tgc caa gct     1167
Glu His Tyr Lys Lys Leu Tyr Arg Ser Val Phe Gly Lys Cys Gln Ala
                350                 355                 360

tta tgg aat aaa agc agc cga tcg gct cta gca gct gaa gct gtt gaa     1215
Leu Trp Asn Lys Ser Ser Arg Ser Ala Leu Ala Ala Glu Ala Val Glu
            365                 370                 375
```

```
tca gaa agc cgg ctt cag ctt tta agg cca aac caa acg cgg tgg aat     1263
Ser Glu Ser Arg Leu Gln Leu Leu Arg Pro Asn Gln Thr Arg Trp Asn
        380                 385                 390

tca act ttt atg gct gtt gac aga att ctt caa att tgc aaa gaa gca     1311
Ser Thr Phe Met Ala Val Asp Arg Ile Leu Gln Ile Cys Lys Glu Ala
    395                 400                 405

gga gaa ggc gca ctt cgg aat ata tgc acc tct ctt gag gtt cca atg     1359
Gly Glu Gly Ala Leu Arg Asn Ile Cys Thr Ser Leu Glu Val Pro Met
410                 415                 420                 425

ttt aat cca gca gaa atg ctg ttc ttg aca gag tgg gcc aac aca atg     1407
Phe Asn Pro Ala Glu Met Leu Phe Leu Thr Glu Trp Ala Asn Thr Met
                430                 435                 440

cgt cca gtt gca aaa gta ctc gac atc ttg caa gcg gaa acg aat aca     1455
Arg Pro Val Ala Lys Val Leu Asp Ile Leu Gln Ala Glu Thr Asn Thr
            445                 450                 455

cag ctg ggg tgg ctg ctg cct agt gtc cat cag tta agc ttg aaa ctt     1503
Gln Leu Gly Trp Leu Leu Pro Ser Val His Gln Leu Ser Leu Lys Leu
        460                 465                 470

cag cga ctc cac cat tct ctc agg tac tgt gac cca ctt gtg gat gcc     1551
Gln Arg Leu His His Ser Leu Arg Tyr Cys Asp Pro Leu Val Asp Ala
    475                 480                 485

cta caa caa gga atc caa aca cga ttc aag cat atg ttt gaa gat cct     1599
Leu Gln Gln Gly Ile Gln Thr Arg Phe Lys His Met Phe Glu Asp Pro
490                 495                 500                 505

gag atc ata gca gct gcc atc ctt ctc cct aaa ttt cgg acc tct tgg     1647
Glu Ile Ile Ala Ala Ala Ile Leu Leu Pro Lys Phe Arg Thr Ser Trp
                510                 515                 520

aca aat gat gaa acc atc ata aaa cga ggc atg gac tac atc aga gtg     1695
Thr Asn Asp Glu Thr Ile Ile Lys Arg Gly Met Asp Tyr Ile Arg Val
            525                 530                 535

cat ctg gag cct ttg gac cac aag aag gaa ttg gcc aac agt tca tct     1743
His Leu Glu Pro Leu Asp His Lys Lys Glu Leu Ala Asn Ser Ser Ser
        540                 545                 550

gat gat gaa gat ttt ttc gct tct ttg aaa ccg aca aca cat gaa gcc     1791
Asp Asp Glu Asp Phe Phe Ala Ser Leu Lys Pro Thr Thr His Glu Ala
    555                 560                 565

agc aaa gag ttg gat gga tat ctg gcc tgt gtt tca gac acc agg gag     1839
Ser Lys Glu Leu Asp Gly Tyr Leu Ala Cys Val Ser Asp Thr Arg Glu
570                 575                 580                 585

tct ctg ctc acg ttt cct gct att tgc agc ctc tct atc aag act aat     1887
Ser Leu Leu Thr Phe Pro Ala Ile Cys Ser Leu Ser Ile Lys Thr Asn
                590                 595                 600

aca cct ctt ccc gca tcg gct gcc tgt gag agg ctt ttc agc act gca     1935
Thr Pro Leu Pro Ala Ser Ala Ala Cys Glu Arg Leu Phe Ser Thr Ala
            605                 610                 615

gga ttg ctt ttc agc ccc aaa aga gct agg ctt gac act aac aat ttt     1983
Gly Leu Leu Phe Ser Pro Lys Arg Ala Arg Leu Asp Thr Asn Asn Phe
        620                 625                 630

gag aat cag ctt cta ctg aag tta aat ctg agg ttt tac aac ttt gag     2031
Glu Asn Gln Leu Leu Leu Lys Leu Asn Leu Arg Phe Tyr Asn Phe Glu
    635                 640                 645

tag cgtgtactgg cattagattg tctgtcttat agtttgataa ttaaatacaa          2084

acagttctaa agcaggataa aaccttgtat gcatttcatt taatgttttt tgagattaaa   2144

agcttaaaca ag                                                       2156
```

<210> SEQ ID NO 5
<211> LENGTH: 649
<212> TYPE: PRT
<213> ORGANISM: Oryzias latipes

<400> SEQUENCE: 5

```
Met Glu Glu Val Cys Asp Ser Ser Ala Ala Ala Ser Ser Thr Val Gln
1               5                   10                  15

Asn Gln Pro Gln Asp Gln Glu His Pro Trp Pro Tyr Leu Arg Glu Phe
            20                  25                  30

Phe Ser Leu Ser Gly Val Asn Lys Asp Ser Phe Lys Met Lys Cys Val
        35                  40                  45

Leu Cys Leu Pro Leu Asn Lys Glu Ile Ser Ala Phe Lys Ser Ser Pro
    50                  55                  60

Ser Asn Leu Arg Lys His Ile Glu Arg Met His Pro Asn Tyr Leu Lys
65                  70                  75                  80

Asn Tyr Ser Lys Leu Thr Ala Gln Lys Arg Lys Ile Gly Thr Ser Thr
                85                  90                  95

His Ala Ser Ser Ser Lys Gln Leu Lys Val Asp Ser Val Phe Pro Val
            100                 105                 110

Lys His Val Ser Pro Val Thr Val Asn Lys Ala Ile Leu Arg Tyr Ile
        115                 120                 125

Ile Gln Gly Leu His Pro Phe Ser Thr Val Asp Leu Pro Ser Phe Lys
    130                 135                 140

Glu Leu Ile Ser Thr Leu Gln Pro Gly Ile Ser Val Ile Thr Arg Pro
145                 150                 155                 160

Thr Leu Arg Ser Lys Ile Ala Glu Ala Ala Leu Ile Met Lys Gln Lys
                165                 170                 175

Val Thr Ala Ala Met Ser Glu Val Glu Trp Ile Ala Thr Thr Thr Asp
            180                 185                 190

Cys Trp Thr Ala Arg Arg Lys Ser Phe Ile Gly Val Thr Ala His Trp
        195                 200                 205

Ile Asn Pro Gly Ser Leu Glu Arg His Ser Ala Ala Leu Ala Cys Lys
    210                 215                 220

Arg Leu Met Gly Ser His Thr Phe Glu Val Leu Ala Ser Ala Met Asn
225                 230                 235                 240

Asp Ile His Ser Glu Tyr Glu Ile Arg Asp Lys Val Val Cys Thr Thr
                245                 250                 255

Thr Asp Ser Gly Ser Asn Phe Met Lys Ala Phe Arg Val Phe Gly Val
            260                 265                 270

Glu Asn Asn Asp Ile Glu Thr Glu Ala Arg Arg Cys Glu Ser Asp Asp
        275                 280                 285

Thr Asp Ser Glu Gly Cys Gly Glu Gly Ser Asp Gly Val Glu Phe Gln
    290                 295                 300

Asp Ala Ser Arg Val Leu Asp Gln Asp Asp Gly Phe Glu Phe Gln Leu
305                 310                 315                 320

Pro Lys His Gln Lys Cys Ala Cys His Leu Leu Asn Leu Val Ser Ser
                325                 330                 335

Val Asp Ala Gln Lys Ala Leu Ser Asn Glu His Tyr Lys Lys Leu Tyr
            340                 345                 350

Arg Ser Val Phe Gly Lys Cys Gln Ala Leu Trp Asn Lys Ser Ser Arg
        355                 360                 365

Ser Ala Leu Ala Ala Glu Ala Val Glu Ser Glu Ser Arg Leu Gln Leu
    370                 375                 380

Leu Arg Pro Asn Gln Thr Arg Trp Asn Ser Thr Phe Met Ala Val Asp
385                 390                 395                 400

Arg Ile Leu Gln Ile Cys Lys Glu Ala Gly Glu Gly Ala Leu Arg Asn
```

```
                405                 410                 415

Ile Cys Thr Ser Leu Glu Val Pro Met Phe Asn Pro Ala Glu Met Leu
            420                 425                 430

Phe Leu Thr Glu Trp Ala Asn Thr Met Arg Pro Val Ala Lys Val Leu
        435                 440                 445

Asp Ile Leu Gln Ala Glu Thr Asn Thr Gln Leu Gly Trp Leu Leu Pro
    450                 455                 460

Ser Val His Gln Leu Ser Leu Lys Leu Gln Arg Leu His His Ser Leu
465                 470                 475                 480

Arg Tyr Cys Asp Pro Leu Val Asp Ala Leu Gln Gln Gly Ile Gln Thr
                485                 490                 495

Arg Phe Lys His Met Phe Glu Asp Pro Glu Ile Ile Ala Ala Ala Ile
            500                 505                 510

Leu Leu Pro Lys Phe Arg Thr Ser Trp Thr Asn Asp Glu Thr Ile Ile
        515                 520                 525

Lys Arg Gly Met Asp Tyr Ile Arg Val His Leu Glu Pro Leu Asp His
    530                 535                 540

Lys Lys Glu Leu Ala Asn Ser Ser Ser Asp Asp Glu Asp Phe Phe Ala
545                 550                 555                 560

Ser Leu Lys Pro Thr Thr His Glu Ala Ser Lys Glu Leu Asp Gly Tyr
                565                 570                 575

Leu Ala Cys Val Ser Asp Thr Arg Glu Ser Leu Leu Thr Phe Pro Ala
            580                 585                 590

Ile Cys Ser Leu Ser Ile Lys Thr Asn Thr Pro Leu Pro Ala Ser Ala
        595                 600                 605

Ala Cys Glu Arg Leu Phe Ser Thr Ala Gly Leu Leu Phe Ser Pro Lys
    610                 615                 620

Arg Ala Arg Leu Asp Thr Asn Asn Phe Glu Asn Gln Leu Leu Leu Lys
625                 630                 635                 640

Leu Asn Leu Arg Phe Tyr Asn Phe Glu
                645


<210> SEQ ID NO 6
<211> LENGTH: 4682
<212> TYPE: DNA
<213> ORGANISM: Oryzias latipes

<400> SEQUENCE: 6

cagaggtgta aagtacttga gtaattttac ttgattactg tacttaagta ttatttttgg      60

ggatttttac tttacttgag tacaattaaa aatcaatact tttactttta cttaattaca     120

tttttttaga aaaaaaagta ctttttactc cttacaattt tatttacagt caaaaagtac     180

ttattttttg gagatcactt cattctattt tcccttgcta ttaccaaacc aattgaattg     240

cgctgatgcc cagtttaatt taaatgttat ttattctgcc tatgaaaatc gttttcacat     300

tatatgaaat tggtcagaca tgttcattgg tcctttggaa gtgacgtcat gtcacatcta     360

ttaccacaat gcacagcacc ttgacctgga aattagggaa attataacag tcaatcagtg     420

gaagaaaatg gaggaagtat gtgattcatc agcagctgcg agcagcacag tccaaaatca     480

gccacaggat caagagcacc cgtggccgta tcttcgcgaa ttcttttctt taagtggtgt     540

aaataaagat tcattcaaga tgaaatgtgt cctctgtctc ccgcttaata aagaaatatc     600

ggccttcaaa agttcgccat caaacctaag gaagcatatt gaggtaagta cattaagtat     660

tttgttttac tgatagtttt tttttttttt tttttttttt tttttgggtg tgcatgtttt     720
```

```
gacgttgatg gcgcgccttt tatatgtgta gtaggcctat tttcactaat gcatgcgatt    780
gacaatataa ggctcacgta ataaaatgct aaaatgcatt tgtaattggt aacgttaggt    840
ccacgggaaa tttggcgcct attgcagctt tgaataatca ttatcattcc gtgctctcat    900
tgtgtttgaa ttcatgcaaa acacaagaaa accaagcgag aaattttttt ccaaacatgt    960
tgtattgtca aaacggtaac actttacaat gaggttgatt agttcatgta ttaactaaca   1020
ttaaataacc atgagcaata catttgttac tgtatctgtt aatctttgtt aacgttagtt   1080
aatagaaata cagatgttca ttgtttgttc atgttagttc acagtgcatt aactaatgtt   1140
aacaagatat aaagtattag taaatgttga aattaacatg tatacgtgca gttcattatt   1200
agttcatgtt aactaatgta gttaactaac gaaccttatt gtaaaagtgt taccatcaaa   1260
actaatgtaa tgaaatcaat tcaccctgtc atgtcagcct tacagtcctg tgtttttgtc   1320
aatataatca gaaataaaat taatgtttga ttgtcactaa atgctactgt atttctaaaa   1380
tcaacaagta tttaacatta taaagtgtgc aattggctgc aaatgtcagt tttattaaag   1440
ggttagttca cccaaaaatg aaaataatgt cattaatgac tcgccctcat gtcgttccaa   1500
gcccgtaaga cctccgttca tcttcagaac acagtttaag atattttaga tttagtccga   1560
gagctttctg tgcctccatt gagaatgtat gtacggtata ctgtccatgt ccagaaaggt   1620
aataaaaaca tcaaagtagt ccatgtgaca tcagtgggtt agttagaatt ttttgaagca   1680
tcgaatacat tttggtccaa aaataacaaa acctacgact ttattcggca ttgtattctc   1740
ttccgggtct gttgtcaatc cgcgttcacg acttcgcagt gacgctacaa tgctgaataa   1800
agtcgtaggt tttgttattt ttggaccaaa atgtattttc gatgcttcaa ataattctac   1860
ctaacccact gatgtcacat ggactacttt gatgttttta ttacctttct ggacatggac   1920
agtataccgt acatacattt tcagtggagg gacagaaagc tctcggacta aatctaaaat   1980
atcttaaact gtgttccgaa gatgaacgga ggtgttacgg gcttggaacg acatgagggt   2040
gagtcattaa tgacatcttt tcatttttgg gtgaactaac cctttaatgc tgtaatcaga   2100
gagtgtatgt gtaattgtta catttattgc atacaatata aatatttatt tgttgttttt   2160
acagagaatg cacccaaatt acctcaaaaa ctactctaaa ttgacagcac agaagagaaa   2220
gatcgggacc tccacccatg cttccagcag taagcaactg aaagttgact cagttttccc   2280
agtcaaacat gtgtctccag tcactgtgaa caaagctata ttaaggtaca tcattcaagg   2340
acttcatcct ttcagcactg ttgatctgcc atcatttaaa gagctgatta gtacactgca   2400
gcctggcatt tctgtcatta caaggcctac tttacgctcc aagatagctg aagctgctct   2460
gatcatgaaa cagaaagtga ctgctgccat gagtgaagtt gaatggattg caaccacaac   2520
ggattgttgg actgcacgta gaaagtcatt cattggtgta actgctcact ggatcaaccc   2580
tggaagtctt gaaagacatt ccgctgcact tgcctgcaaa agattaatgg gctctcatac   2640
ttttgaggta ctggccagtg ccatgaatga tatccactca gagtatgaaa tacgtgacaa   2700
ggttgtttgc acaaccacag acagtggttc caactttatg aaggctttca gagtttttgg   2760
tgtggaaaac aatgatatcg agactgaggc aagaaggtgt gaaagtgatg acactgattc   2820
tgaaggctgt ggtgagggaa gtgatggtgt ggaattccaa gatgcctcac gagtcctgga   2880
ccaagacgat ggcttcgaat tccagctacc aaaacatcaa aagtgtgcct gtcacttact   2940
taacctagtc tcaagcgttg atgcccaaaa agctctctca aatgaacact acaagaaact   3000
ctacagatct gtctttggca aatgccaagc tttatggaat aaaagcagcc gatcggctct   3060
agcagctgaa gctgttgaat cagaaagccg gcttcagctt ttaaggccaa accaaacgcg   3120
```

```
gtggaattca acttttatgg ctgttgacag aattcttcaa atttgcaaag aagcaggaga   3180
aggcgcactt cggaatatat gcacctctct tgaggttcca atgtaagtgt ttttcccctc   3240
tatcgatgta aacaaatgtg ggttgttttt gtttaatact ctttgattat gctgatttct   3300
cctgtaggtt taatccagca gaaatgctgt tcttgacaga gtgggccaac acaatgcgtc   3360
cagttgcaaa agtactcgac atcttgcaag cggaaacgaa tacacagctg gggtggctgc   3420
tgcctagtgt ccatcagtta agcttgaaac ttcagcgact ccaccattct ctcaggtact   3480
gtgacccact tgtggatgcc ctacaacaag gaatccaaac acgattcaag catatgtttg   3540
aagatcctga gatcatagca gctgccatcc ttctccctaa atttcggacc tcttggacaa   3600
atgatgaaac catcataaaa cgaggtaaat gaatgcaagc aacatacact tgacgaattc   3660
taatctgggc aacctttgag ccataccaaa attattcttt tatttattta tttttgcact   3720
ttttaggaat gttatatccc atctttggct gtgatctcaa tatgaatatt gatgtaaagt   3780
attcttgcag caggttgtag ttatccctca gtgtttcttg aaaccaaact catatgtatc   3840
atatgtggtt tggaaatgca gttagatttt atgctaaaat aagggatttg catgatttta   3900
gatgtagatg actgcacgta aatgtagtta atgacaaaat ccataaaatt tgttcccagt   3960
cagaagcccc tcaaccaaac ttttctttgt gtctgctcac tgtgcttgta ggcatggact   4020
acatcagagt gcatctggag cctttggacc acaagaagga attggccaac agttcatctg   4080
atgatgaaga tttttcgct tctttgaaac cgacaacaca tgaagccagc aaagagttgg   4140
atggatatct ggcctgtgtt tcagacacca gggagtctct gctcacgttt cctgctattt   4200
gcagcctctc tatcaagact aatacacctc ttcccgcatc ggctgcctgt gagaggcttt   4260
tcagcactgc aggattgctt ttcagcccca aaagagctag gcttgacact aacaattttg   4320
agaatcagct tctactgaag ttaaatctga ggttttacaa ctttgagtag cgtgtactgg   4380
cattagattg tctgtcttat agtttgataa ttaaatacaa acagttctaa agcaggataa   4440
aaccttgtat gcatttcatt taatgttttt tgagattaaa agcttaaaca agaatctcta   4500
gtttctttc ttgcttttac ttttacttcc ttaatactca agtacaattt taatggagta   4560
ctttttact tttactcaag taagattcta gccagatact tttactttta attgagtaaa   4620
attttcccta agtacttgta ctttcacttg agtaaaattt ttgagtactt tttacacctc   4680
tg                                                                  4682
```

<210> SEQ ID NO 7
<211> LENGTH: 321
<212> TYPE: DNA
<213> ORGANISM: Artificial
<220> FEATURE:
<223> OTHER INFORMATION: Synthetic construct of Cycloheximide resistant gene
<220> FEATURE:
<221> NAME/KEY: CDS
<222> LOCATION: (1)..(321)

<400> SEQUENCE: 7

```
atg gtc aac gta cct aaa acc cga aga acc ttc tgt aag aag tgt ggc      48
Met Val Asn Val Pro Lys Thr Arg Arg Thr Phe Cys Lys Lys Cys Gly
1               5                   10                  15

aag cat cag cct cac aaa gtg aca cag tat aag aag ggc aag gat tct      96
Lys His Gln Pro His Lys Val Thr Gln Tyr Lys Lys Gly Lys Asp Ser
            20                  25                  30

ttg tat gcc cag gga agg agg cgc tat gat cgg aag cag agt ggc tat     144
Leu Tyr Ala Gln Gly Arg Arg Arg Tyr Asp Arg Lys Gln Ser Gly Tyr
```

```
        35                  40                  45

ggt ggg cag aca aag caa att ttc cgg aag aag gct aag acc aca aag      192
Gly Gly Gln Thr Lys Gln Ile Phe Arg Lys Lys Ala Lys Thr Thr Lys
    50                  55                  60

aag att gtg cta agg ctg gaa tgt gtt gag cct aac tgc aga tcc aag      240
Lys Ile Val Leu Arg Leu Glu Cys Val Glu Pro Asn Cys Arg Ser Lys
65                  70                  75                  80

agg atg ctg gcc att aag aga tgc aag cat ttt gaa ctg gga gga gat      288
Arg Met Leu Ala Ile Lys Arg Cys Lys His Phe Glu Leu Gly Gly Asp
                85                  90                  95

aag aag aga aag ggc caa gtg atc cag ttc taa                          321
Lys Lys Arg Lys Gly Gln Val Ile Gln Phe
            100                 105


<210> SEQ ID NO 8
<211> LENGTH: 106
<212> TYPE: PRT
<213> ORGANISM: Artificial
<220> FEATURE:
<223> OTHER INFORMATION: Synthetic Construct

<400> SEQUENCE: 8

Met Val Asn Val Pro Lys Thr Arg Arg Thr Phe Cys Lys Lys Cys Gly
1               5                   10                  15

Lys His Gln Pro His Lys Val Thr Gln Tyr Lys Lys Gly Lys Asp Ser
            20                  25                  30

Leu Tyr Ala Gln Gly Arg Arg Arg Tyr Asp Arg Lys Gln Ser Gly Tyr
        35                  40                  45

Gly Gly Gln Thr Lys Gln Ile Phe Arg Lys Lys Ala Lys Thr Thr Lys
    50                  55                  60

Lys Ile Val Leu Arg Leu Glu Cys Val Glu Pro Asn Cys Arg Ser Lys
65                  70                  75                  80

Arg Met Leu Ala Ile Lys Arg Cys Lys His Phe Glu Leu Gly Gly Asp
                85                  90                  95

Lys Lys Arg Lys Gly Gln Val Ile Gln Phe
            100                 105


<210> SEQ ID NO 9
<211> LENGTH: 1404
<212> TYPE: DNA
<213> ORGANISM: Artificial
<220> FEATURE:
<223> OTHER INFORMATION: Synthetic construct of M2Z3 Heavy chain
<220> FEATURE:
<221> NAME/KEY: CDS
<222> LOCATION: (1)..(1404)

<400> SEQUENCE: 9

atg gac tgg acc tgg agc atc ctt ttc ttg gtg gca gca gca aca ggt       48
Met Asp Trp Thr Trp Ser Ile Leu Phe Leu Val Ala Ala Ala Thr Gly
1               5                   10                  15

gcc cac tcc cag gtt cag ctg gtg cag tct gga gct gag gtg aag aag       96
Ala His Ser Gln Val Gln Leu Val Gln Ser Gly Ala Glu Val Lys Lys
            20                  25                  30

cct ggg gcc tca gtg aag gtc tcc tgc aag gct tct ggt tac acc ttt      144
Pro Gly Ala Ser Val Lys Val Ser Cys Lys Ala Ser Gly Tyr Thr Phe
        35                  40                  45

acc agc tat ggt atc agc tgg gtg cga cag gcc cct gga caa ggg ctt      192
Thr Ser Tyr Gly Ile Ser Trp Val Arg Gln Ala Pro Gly Gln Gly Leu
    50                  55                  60

gag tgg atg gga tgg atc agc gct tac aat ggt aac aca aac tat gca      240
```

-continued

```
Glu Trp Met Gly Trp Ile Ser Ala Tyr Asn Gly Asn Thr Asn Tyr Ala
65                  70                  75                  80

cag aag ctc cag ggc aga gtc acc atg acc aca gac aca tcc acg agc      288
Gln Lys Leu Gln Gly Arg Val Thr Met Thr Thr Asp Thr Ser Thr Ser
                85                  90                  95

aca gcc tac atg gag ctg agg agc ctg aga tct gac gac acg gcc gtg      336
Thr Ala Tyr Met Glu Leu Arg Ser Leu Arg Ser Asp Asp Thr Ala Val
            100                 105                 110

tat tac tgt gcg agg gca gca gct ggc gga tac ttc cag cac tgg ggc      384
Tyr Tyr Cys Ala Arg Ala Ala Ala Gly Gly Tyr Phe Gln His Trp Gly
        115                 120                 125

cag ggc acc ctg gtc acc gtc tcc tca gct agc acc aag ggc cca tcg      432
Gln Gly Thr Leu Val Thr Val Ser Ser Ala Ser Thr Lys Gly Pro Ser
    130                 135                 140

gtc ttc ccc ctg gca ccc tcc tcc aag agc acc tct ggg ggc aca gcg      480
Val Phe Pro Leu Ala Pro Ser Ser Lys Ser Thr Ser Gly Gly Thr Ala
145                 150                 155                 160

gcc ctg ggc tgc ctg gtc aag gac tac ttc ccc gaa ccg gtg acg gtg      528
Ala Leu Gly Cys Leu Val Lys Asp Tyr Phe Pro Glu Pro Val Thr Val
                165                 170                 175

tcg tgg aac tca ggc gcc ctg acc agc ggc gtg cac acc ttc ccg gct      576
Ser Trp Asn Ser Gly Ala Leu Thr Ser Gly Val His Thr Phe Pro Ala
            180                 185                 190

gtc cta cag tcc tca gga ctc tac tcc ctc agc agc gtg gtg acc gtg      624
Val Leu Gln Ser Ser Gly Leu Tyr Ser Leu Ser Ser Val Val Thr Val
        195                 200                 205

ccc tcc agc agc ttg ggc acc cag acc tac atc tgc aac gtg aat cac      672
Pro Ser Ser Ser Leu Gly Thr Gln Thr Tyr Ile Cys Asn Val Asn His
    210                 215                 220

aag ccc agc aac acc aag gtg gac aag aaa gtt gag ccc aaa tct tgt      720
Lys Pro Ser Asn Thr Lys Val Asp Lys Lys Val Glu Pro Lys Ser Cys
225                 230                 235                 240

gac aaa act cac aca tgc cca ccg tgc cca gca cct gaa ctc ctg ggg      768
Asp Lys Thr His Thr Cys Pro Pro Cys Pro Ala Pro Glu Leu Leu Gly
                245                 250                 255

gga ccg tca gtc ttc ctc ttc ccc cca aaa ccc aag gac acc ctc atg      816
Gly Pro Ser Val Phe Leu Phe Pro Pro Lys Pro Lys Asp Thr Leu Met
            260                 265                 270

atc tcc cgg acc cct gag gtc aca tgc gtg gtg gtg gac gtg agc cac      864
Ile Ser Arg Thr Pro Glu Val Thr Cys Val Val Val Asp Val Ser His
        275                 280                 285

gaa gac cct gag gtc aag ttc aac tgg tac gtg gac ggc gtg gag gtg      912
Glu Asp Pro Glu Val Lys Phe Asn Trp Tyr Val Asp Gly Val Glu Val
    290                 295                 300

cat aat gcc aag aca aag ccg cgg gag gag cag tac aac agc acg tac      960
His Asn Ala Lys Thr Lys Pro Arg Glu Glu Gln Tyr Asn Ser Thr Tyr
305                 310                 315                 320

cgt gtg gtc agc gtc ctc acc gtc ctg cac cag gac tgg ctg aat ggc     1008
Arg Val Val Ser Val Leu Thr Val Leu His Gln Asp Trp Leu Asn Gly
                325                 330                 335

aag gag tac aag tgc aag gtc tcc aac aaa gcc ctc cca gcc ccc atc     1056
Lys Glu Tyr Lys Cys Lys Val Ser Asn Lys Ala Leu Pro Ala Pro Ile
            340                 345                 350

gag aaa acc atc tcc aaa gcc aaa ggg cag ccc cga gaa cca cag gtg     1104
Glu Lys Thr Ile Ser Lys Ala Lys Gly Gln Pro Arg Glu Pro Gln Val
        355                 360                 365

tac acc ctg ccc cca tcc cgg gat gag ctg acc aag aac cag gtc agc     1152
Tyr Thr Leu Pro Pro Ser Arg Asp Glu Leu Thr Lys Asn Gln Val Ser
    370                 375                 380
```

```
ctg acc tgc ctg gtc aaa ggc ttc tat ccc agc gac atc gcc gtg gag      1200
Leu Thr Cys Leu Val Lys Gly Phe Tyr Pro Ser Asp Ile Ala Val Glu
385                 390                 395                 400

tgg gag agc aat ggg cag ccg gag aac aac tac aag acc acg cct ccc      1248
Trp Glu Ser Asn Gly Gln Pro Glu Asn Asn Tyr Lys Thr Thr Pro Pro
                405                 410                 415

gtg ctg gac tcc gac ggc tcc ttc ttc ctc tac agc aag ctc acc gtg      1296
Val Leu Asp Ser Asp Gly Ser Phe Phe Leu Tyr Ser Lys Leu Thr Val
            420                 425                 430

gac aag agc agg tgg cag cag ggg aac gtc ttc tca tgc tcc gtg atg      1344
Asp Lys Ser Arg Trp Gln Gln Gly Asn Val Phe Ser Cys Ser Val Met
        435                 440                 445

cat gag gct ctg cac aac cac tac acg cag aag agc ctc tcc ctg tct      1392
His Glu Ala Leu His Asn His Tyr Thr Gln Lys Ser Leu Ser Leu Ser
    450                 455                 460

ccg ggt aaa tga                                                      1404
Pro Gly Lys
465


<210> SEQ ID NO 10
<211> LENGTH: 467
<212> TYPE: PRT
<213> ORGANISM: Artificial
<220> FEATURE:
<223> OTHER INFORMATION: Synthetic Construct

<400> SEQUENCE: 10

Met Asp Trp Thr Trp Ser Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Gly Ile Ser Trp Val Arg Gln Ala Pro Gly Gln Gly Leu
    50                  55                  60

Glu Trp Met Gly Trp Ile Ser Ala Tyr Asn Gly Asn Thr Asn Tyr Ala
65                  70                  75                  80

Gln Lys Leu Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Ala Ala Ala Gly Gly Tyr Phe Gln His Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240
```

```
Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465


<210> SEQ ID NO 11
<211> LENGTH: 708
<212> TYPE: DNA
<213> ORGANISM: Artificial
<220> FEATURE:
<223> OTHER INFORMATION: Synthetic construct of M2Z3 Light chian
<220> FEATURE:
<221> NAME/KEY: CDS
<222> LOCATION: (1)..(708)

<400> SEQUENCE: 11

atg gcc agc ttc cct ctc ctc ctc acc ctc ctc act cac tgt gca ggg       48
Met Ala Ser Phe Pro Leu Leu Leu Thr Leu Leu Thr His Cys Ala Gly
1               5                   10                  15

tcc tgg gcc cag tct gtg ctg act cag cca ccc tca gcg tct ggg acc       96
Ser Trp Ala Gln Ser Val Leu Thr Gln Pro Pro Ser Ala Ser Gly Thr
            20                  25                  30

ccc ggg cag agg gtc acc atc tct tgt tct gga agc aac tcc aac atc      144
Pro Gly Gln Arg Val Thr Ile Ser Cys Ser Gly Ser Asn Ser Asn Ile
        35                  40                  45

gga agt aaa act gta aac tgg tac cag cag ctc cca gga acg gcc ccc      192
Gly Ser Lys Thr Val Asn Trp Tyr Gln Gln Leu Pro Gly Thr Ala Pro
    50                  55                  60

aaa ctc ctc atc tct agt aat aat cag cgg ccc tca ggg gtc cct gac      240
Lys Leu Leu Ile Ser Ser Asn Asn Gln Arg Pro Ser Gly Val Pro Asp
65                  70                  75                  80

cga ttc tct ggc tcc aag tct ggc acc tca gcc tcc ctg gcc atc agt      288
```

```
Arg Phe Ser Gly Ser Lys Ser Gly Thr Ser Ala Ser Leu Ala Ile Ser
                85                  90                  95

ggg ctc cag tct gag gat gag gct gat tat tac tgt gca gca tgg gat      336
Gly Leu Gln Ser Glu Asp Glu Ala Asp Tyr Tyr Cys Ala Ala Trp Asp
            100                 105                 110

gac agc ctg aat ggt gtg gta ttc ggc gga ggg acc aag ctg acc gtc      384
Asp Ser Leu Asn Gly Val Val Phe Gly Gly Gly Thr Lys Leu Thr Val
        115                 120                 125

cta ggt cag ccc aag gct gcc ccc tcg gtc act ctg ttc cca ccc tcc      432
Leu Gly Gln Pro Lys Ala Ala Pro Ser Val Thr Leu Phe Pro Pro Ser
    130                 135                 140

tct gag gag ctt caa gcc aac aag gcc aca ctg gtg tgt ctc ata agt      480
Ser Glu Glu Leu Gln Ala Asn Lys Ala Thr Leu Val Cys Leu Ile Ser
145                 150                 155                 160

gac ttc tac ccg gga gcc gtg aca gtg gcc tgg aag gca gat agc agc      528
Asp Phe Tyr Pro Gly Ala Val Thr Val Ala Trp Lys Ala Asp Ser Ser
                165                 170                 175

ccc gtc aag gcg gga gtg gag acc acc aca ccc tcc aaa caa agc aac      576
Pro Val Lys Ala Gly Val Glu Thr Thr Thr Pro Ser Lys Gln Ser Asn
            180                 185                 190

aac aag tac gcg gcc agc agc tac ctg agc ctg acg cct gag cag tgg      624
Asn Lys Tyr Ala Ala Ser Ser Tyr Leu Ser Leu Thr Pro Glu Gln Trp
        195                 200                 205

aag tcc cac aaa agc tac agc tgc cag gtc acg cat gaa ggg agc acc      672
Lys Ser His Lys Ser Tyr Ser Cys Gln Val Thr His Glu Gly Ser Thr
    210                 215                 220

gtg gag aag aca gtg gcc cct aca gaa tgt tca tag                      708
Val Glu Lys Thr Val Ala Pro Thr Glu Cys Ser
225                 230                 235


<210> SEQ ID NO 12
<211> LENGTH: 235
<212> TYPE: PRT
<213> ORGANISM: Artificial
<220> FEATURE:
<223> OTHER INFORMATION: Synthetic Construct

<400> SEQUENCE: 12

Met Ala Ser Phe Pro Leu Leu Leu Thr Leu Leu Thr His Cys Ala Gly
1               5                   10                  15

Ser Trp Ala Gln Ser Val Leu Thr Gln Pro Pro Ser Ala Ser Gly Thr
            20                  25                  30

Pro Gly Gln Arg Val Thr Ile Ser Cys Ser Gly Ser Asn Ser Asn Ile
        35                  40                  45

Gly Ser Lys Thr Val Asn Trp Tyr Gln Gln Leu Pro Gly Thr Ala Pro
    50                  55                  60

Lys Leu Leu Ile Ser Ser Asn Asn Gln Arg Pro Ser Gly Val Pro Asp
65                  70                  75                  80

Arg Phe Ser Gly Ser Lys Ser Gly Thr Ser Ala Ser Leu Ala Ile Ser
                85                  90                  95

Gly Leu Gln Ser Glu Asp Glu Ala Asp Tyr Tyr Cys Ala Ala Trp Asp
            100                 105                 110

Asp Ser Leu Asn Gly Val Val Phe Gly Gly Gly Thr Lys Leu Thr Val
        115                 120                 125

Leu Gly Gln Pro Lys Ala Ala Pro Ser Val Thr Leu Phe Pro Pro Ser
    130                 135                 140

Ser Glu Glu Leu Gln Ala Asn Lys Ala Thr Leu Val Cys Leu Ile Ser
145                 150                 155                 160
```

```
Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Lys Ser Tyr Ser Cys Gln Val Thr His Glu Gly Ser Thr
    210                 215                 220

Val Glu Lys Thr Val Ala Pro Thr Glu Cys Ser
225                 230                 235


<210> SEQ ID NO 13
<211> LENGTH: 1855
<212> TYPE: DNA
<213> ORGANISM: artificial
<220> FEATURE:
<223> OTHER INFORMATION: Synthetic construct of nonautologus Tol1
      transposon

<400> SEQUENCE: 13

cagtagcggt tctaggcacg ggccgtccgg gcggtggcct ggggcggaaa actgaagggg     60

ggcggcaccg gcggctcagc cctttgtaat atattaatat gcaccactat tggtttactt    120

atgtcacagt ttgtaagttt gtaacagcct gaacctggcc gcgccgccgc cctcgccccg    180

cagctgcgct ctcctgtctt tgagaagtag acacaaatgt gtgtgaagaa ggagaaggga    240

gggggcgcgg ggtgagcacg gagcgtcgcc gcgtttgcgc atgcgcaaaa cctggctggc    300

tcatctttca ggggaggcga cggtcgcggg cttgatgaaa aaaataaaag taaaaactgc    360

gactgcgccg tcatgtagcg aatcagcgcc cctggctgta gctgcacgcg ctcctgctgg    420

aaatgtgtga agaggggggg gggggggggg gctgcgggga atcagttcaa ttgtgggacg    480

cttccaaatt aagtggctag gtggggacaa gggcgggggt ttgaatctac ttcataaaac    540

ctttttatat tataagtcag tcataaggtg acattctata acctacattt taataaaggt    600

ataaaaaata tattctgctt tttttgggtt aattttgtgt gaaatgtcca aataaaaaaa    660

atggcaacac aaaacaatgc tgtcactaag gtgacagttg gttcagtcga cggacttgat    720

gccttcttcg tgacgtgagg acatttatgc caaacaaacg ccaataaaca tctaaaatat    780

ggaaaagaaa aggtcaaagc catctggtgc ccaatttaga aagaaaaagaa aagaagaaga    840

ggagaaaaga gataaagaaa agggtaagtc ctcacagctt gatgcatgtt ttttctaaat    900

tctaatgcta cctgccctac aacaacgttg ccgatgaaaa ctttattttg gtcgatgacc    960

aacactgaat taggcccaaa tgttgcaaat agcgtcattt tttttttttt ttttagattt   1020

tattcttaaa aatttgctct gccttaactt gtaacattag ttatgattca tgtgtctgtc   1080

tgctctgctg taacacaaag gttttgttgg gttttgctgt tgtatactag ctcataatgt   1140

taaaaaagct gtgatggtta cacagcatgc tggtgctgcc ataagatgct aatggggcaa   1200

ataatttgag attggtcatt aatttaataa tcatttgtgg cagcctaaac gttttcacaa   1260

tgttttttttg acatttaact ggggatttag gggttaattt tgagcctgca tatgaagttt   1320

attttttatt tgttttacaa atgtgggatt atatttttag ccaatagaat ttccataaat   1380

ctgtaggtag ttttaaaaat gaatatttac catttactgc aactctatgg ggacaaaaca   1440

taatgtaaca ggtcataact aaaaatgtgc caatcaaagg attgaagacg gaaaacatga   1500

gttaattttt cttctctgaa gtagagatcg atatagaaca tgacaattta aatttccaat   1560

tcataaatgt ttttaaaata tttattttat attatttatt taacattgag tttgattcaa   1620
```

```
tattttctta gctaactgta tttttgccat gcttatggtc ttttattttt tgtgttctga   1680

taacttttat aatgcttttc agaattttga catcttttgt atccacttct taatttcaat   1740

gacaataaaa catttcagtt gacgaagaca aacaaagttc tgttgtgact atgggggggg   1800

ggggcgcctg gggatggtct cgcccgggga gtaattcagg gtagaaccgc cactg        1855


<210> SEQ ID NO 14
<211> LENGTH: 200
<212> TYPE: DNA
<213> ORGANISM: artificial
<220> FEATURE:
<223> OTHER INFORMATION: Synthetic construct of Tol1-L transposon
      sequence

<400> SEQUENCE: 14

cagtagcggt tctaggcacg ggccgtccgg gcggtggcct ggggcggaaa actgaagggg     60

ggcggcaccg gcggctcagc cctttgtaat atattaatat gcaccactat tggtttactt    120

atgtcacagt ttgtaagttt gtaacagcct gaacctggcc gcgccgccgc cctcgccccg    180

cagctgcgct ctcctgtctt                                                200


<210> SEQ ID NO 15
<211> LENGTH: 505
<212> TYPE: DNA
<213> ORGANISM: artificial
<220> FEATURE:
<223> OTHER INFORMATION: Synthetic construct of Tol1-R transoposon
      sequence

<400> SEQUENCE: 15

atatttttag ccaatagaat ttccataaat ctgtaggtag ttttaaaaat gaatatttac     60

catttactgc aactctatgg ggacaaaaca taatgtaaca ggtcataact aaaaatgtgc    120

caatcaaagg attgaagacg gaaaacatga gttaattttt cttctctgaa gtagagatcg    180

atatagaaca tgacaattta aatttccaat tcataaatgt ttttaaaata tttattttat    240

attatttatt taacattgag tttgattcaa tattttctta gctaactgta tttttgccat    300

gcttatggtc ttttattttt tgtgttctga taacttttat aatgcttttc agaattttga    360

catcttttgt atccacttct taatttcaat gacaataaaa catttcagtt gacgaagaca    420

aacaaagttc tgttgtgact atgggggggg ggggcgcctg gggatggtct cgcccgggga    480

gtaattcagg gtagaaccgc cactg                                          505


<210> SEQ ID NO 16
<211> LENGTH: 2745
<212> TYPE: DNA
<213> ORGANISM: Oryzias latipes
<220> FEATURE:
<221> NAME/KEY: CDS
<222> LOCATION: (30)..(2585)

<400> SEQUENCE: 16

gccaaacaaa cgccaaaaac atctaaaat atg gag aaa aaa agg tca aag cca       53
                                Met Glu Lys Lys Arg Ser Lys Pro
                                1               5

tct ggt gcc caa ttt aga aag aaa aga aaa gaa gaa gag gag aaa aga      101
Ser Gly Ala Gln Phe Arg Lys Lys Arg Lys Glu Glu Glu Glu Lys Arg
    10                  15                  20

gat aaa gaa aag ggg gca ctt cta aga tat ttt gga tcg tct acc act      149
Asp Lys Glu Lys Gly Ala Leu Leu Arg Tyr Phe Gly Ser Ser Thr Thr
25                  30                  35                  40
```

```
gct caa gat gag aca tct acc tcc ctg cca gct atc tca tca gcc aca      197
Ala Gln Asp Glu Thr Ser Thr Ser Leu Pro Ala Ile Ser Ser Ala Thr
                45                  50                  55

gtc aca gtc tca ccc cct cag gat gag cta cca tct aca tcc tct gct      245
Val Thr Val Ser Pro Pro Gln Asp Glu Leu Pro Ser Thr Ser Ser Ala
            60                  65                  70

act cat gta gtt cca cag ttg tta cct gag caa agt ttt gat agt gag      293
Thr His Val Val Pro Gln Leu Leu Pro Glu Gln Ser Phe Asp Ser Glu
        75                  80                  85

gct gaa gac gtt gtt cca tct acg tct acc cag ctt gag act tca gaa      341
Ala Glu Asp Val Val Pro Ser Thr Ser Thr Gln Leu Glu Thr Ser Glu
    90                  95                  100

atg cct ggt gat gaa acc cca ctg acc ccg act gct gag gac cag cct      389
Met Pro Gly Asp Glu Thr Pro Leu Thr Pro Thr Ala Glu Asp Gln Pro
105                 110                 115                 120

cta cca act gac cct gca aag tgg ccc tca cct ctg act gac agg ata      437
Leu Pro Thr Asp Pro Ala Lys Trp Pro Ser Pro Leu Thr Asp Arg Ile
                125                 130                 135

cgg atg gag ctg gtt cga aga gga cca agt agc ata cca cct gac ttt      485
Arg Met Glu Leu Val Arg Arg Gly Pro Ser Ser Ile Pro Pro Asp Phe
            140                 145                 150

gtt ttc cca aga aat gac agt gat ggg aga agt tgt cat cac cac tat      533
Val Phe Pro Arg Asn Asp Ser Asp Gly Arg Ser Cys His His His Tyr
        155                 160                 165

ttc agg aag aca cta gta agt ggt gaa aaa ata gca aga act tgg ttg      581
Phe Arg Lys Thr Leu Val Ser Gly Glu Lys Ile Ala Arg Thr Trp Leu
    170                 175                 180

atg tat tca aaa gtg aag aac agc ctc ttt tgc ttt tgt tgc aaa ttg      629
Met Tyr Ser Lys Val Lys Asn Ser Leu Phe Cys Phe Cys Cys Lys Leu
185                 190                 195                 200

ttt tcc aac aaa aac att aat tta aca act tct ggt aca gca aac tgg      677
Phe Ser Asn Lys Asn Ile Asn Leu Thr Thr Ser Gly Thr Ala Asn Trp
                205                 210                 215

aaa cat gca agc aca tac ctc aca gca cac gaa aaa agc cca gaa cac      725
Lys His Ala Ser Thr Tyr Leu Thr Ala His Glu Lys Ser Pro Glu His
            220                 225                 230

ctc aat tgt atg aaa gca tgg aag gaa ctg tca ggg agg atc aga agt      773
Leu Asn Cys Met Lys Ala Trp Lys Glu Leu Ser Gly Arg Ile Arg Ser
        235                 240                 245

ggg aaa aca att gat aag cag gag atg gca ctt ctg gaa gag gag cgg      821
Gly Lys Thr Ile Asp Lys Gln Glu Met Ala Leu Leu Glu Glu Glu Arg
    250                 255                 260

gtg aga tgg aga gca gtg cta acc cgt ctc att gct att gtg cag tca      869
Val Arg Trp Arg Ala Val Leu Thr Arg Leu Ile Ala Ile Val Gln Ser
265                 270                 275                 280

ctg gca gtt cgg aat ttg gct cta agg gga cac aca gaa aca ctg ttc      917
Leu Ala Val Arg Asn Leu Ala Leu Arg Gly His Thr Glu Thr Leu Phe
                285                 290                 295

aca tca tca aat ggg aat ttt ttg aaa gag gtt gaa ctg atg gcc agg      965
Thr Ser Ser Asn Gly Asn Phe Leu Lys Glu Val Glu Leu Met Ala Arg
            300                 305                 310

ttt gat ccc ata atg aaa gat cat ctt aac cgt gta tta aga gga aca     1013
Phe Asp Pro Ile Met Lys Asp His Leu Asn Arg Val Leu Arg Gly Thr
        315                 320                 325

gca agt cac aac agc tac ata ggc cat cat gtg cag aat gaa ctt att     1061
Ala Ser His Asn Ser Tyr Ile Gly His His Val Gln Asn Glu Leu Ile
    330                 335                 340

gat ttg ttg agc agc aaa atc cta tcc gct ata gtg gat gac atc aaa     1109
Asp Leu Leu Ser Ser Lys Ile Leu Ser Ala Ile Val Asp Asp Ile Lys
```

```
345                 350                 355                 360

aag gca aaa tat ttt tca ata att ctg gac tgc act ctg gat ata agc     1157
Lys Ala Lys Tyr Phe Ser Ile Ile Leu Asp Cys Thr Leu Asp Ile Ser
                365                 370                 375

cac aca gaa cag ttg tca gtt ata att aga gtg gtg tca ctg atg gag     1205
His Thr Glu Gln Leu Ser Val Ile Ile Arg Val Val Ser Leu Met Glu
            380                 385                 390

aag cct cag atc agg gaa cat ttt atg ggg ttt ttg gag gca gag gag     1253
Lys Pro Gln Ile Arg Glu His Phe Met Gly Phe Leu Glu Ala Glu Glu
        395                 400                 405

tcc aca ggc cag cac ttg gca tcc atg atc tta aac aga ctt gag gag     1301
Ser Thr Gly Gln His Leu Ala Ser Met Ile Leu Asn Arg Leu Glu Glu
    410                 415                 420

tta gga att tct ttt gaa gac tgc aga gga caa tca tat gat aat ggg     1349
Leu Gly Ile Ser Phe Glu Asp Cys Arg Gly Gln Ser Tyr Asp Asn Gly
425                 430                 435                 440

gca aat atg aaa ggc aaa aat aag gga gta caa gcc agg ctc tta gaa     1397
Ala Asn Met Lys Gly Lys Asn Lys Gly Val Gln Ala Arg Leu Leu Glu
                445                 450                 455

aag aat ccc cgt gct ctg ttt ttg cca tgc ggt gca cac aca ttg aat     1445
Lys Asn Pro Arg Ala Leu Phe Leu Pro Cys Gly Ala His Thr Leu Asn
            460                 465                 470

tta gtt gtg tgt gat gct gct aag aga tct gtt gat gct atg agc tac     1493
Leu Val Val Cys Asp Ala Ala Lys Arg Ser Val Asp Ala Met Ser Tyr
        475                 480                 485

ttt ggt gtc ctg caa aag ctt tac act tta ttt tca gcc tct gcc caa     1541
Phe Gly Val Leu Gln Lys Leu Tyr Thr Leu Phe Ser Ala Ser Ala Gln
    490                 495                 500

cga tgg gcc ata ctg aag agt cag gtg agc atc act cta aag tcg tgg     1589
Arg Trp Ala Ile Leu Lys Ser Gln Val Ser Ile Thr Leu Lys Ser Trp
505                 510                 515                 520

aca gaa aca agg tgg gag agc aaa atc aaa agc atc gag ccc atg agg     1637
Thr Glu Thr Arg Trp Glu Ser Lys Ile Lys Ser Ile Glu Pro Met Arg
                525                 530                 535

tac cag gga gct gca gtg aga gag gct tta ata gaa gtg aga gac aag     1685
Tyr Gln Gly Ala Ala Val Arg Glu Ala Leu Ile Glu Val Arg Asp Lys
            540                 545                 550

acc aaa gac cca gtt ata aag gct gag gcc cag tct ttg tct gaa gag     1733
Thr Lys Asp Pro Val Ile Lys Ala Glu Ala Gln Ser Leu Ser Glu Glu
        555                 560                 565

gta ggg tcg tac cgc ttc aac atc tgc aca gtc gta tgg cat gac att     1781
Val Gly Ser Tyr Arg Phe Asn Ile Cys Thr Val Val Trp His Asp Ile
    570                 575                 580

cta tct aca ata aag cat gtc agc aaa ctc atg cag tct cca aat atg     1829
Leu Ser Thr Ile Lys His Val Ser Lys Leu Met Gln Ser Pro Asn Met
585                 590                 595                 600

cat gtg gac cta gct gtg agt ctt ttg aag aag act gaa caa agt ctc     1877
His Val Asp Leu Ala Val Ser Leu Leu Lys Lys Thr Glu Gln Ser Leu
                605                 610                 615

cag agc tac agg gca aat ggc ttt gtg aat gca cag atg gca gcc aaa     1925
Gln Ser Tyr Arg Ala Asn Gly Phe Val Asn Ala Gln Met Ala Ala Lys
            620                 625                 630

gaa atg tgc aag gaa atg aat gtc gag gct att ttg aaa caa aaa aga     1973
Glu Met Cys Lys Glu Met Asn Val Glu Ala Ile Leu Lys Gln Lys Arg
        635                 640                 645

ata aga tcc aca aag tgc caa ttc tcg tat gaa tca cac gat gag cct     2021
Ile Arg Ser Thr Lys Cys Gln Phe Ser Tyr Glu Ser His Asp Glu Pro
    650                 655                 660

ttc agt gac gca ctt aaa aag ttg gag gtt gaa ttt ttc aat gtt gtt     2069
```

```
Phe Ser Asp Ala Leu Lys Lys Leu Glu Val Glu Phe Phe Asn Val Val
665                 670                 675                 680

gtt gat gaa gcc ttg tca gcc atc gcg gag agg ttt tcc aca ttg gaa      2117
Val Asp Glu Ala Leu Ser Ala Ile Ala Glu Arg Phe Ser Thr Leu Glu
                685                 690                 695

gtt gta caa aac aga ttt ggg gtt ttg acc aat ttc cca agc ctt gga      2165
Val Val Gln Asn Arg Phe Gly Val Leu Thr Asn Phe Pro Ser Leu Gly
            700                 705                 710

gac gag gag ctg acg gag caa tgc gag gca cta ggc aac ata ctc cat      2213
Asp Glu Glu Leu Thr Glu Gln Cys Glu Ala Leu Gly Asn Ile Leu His
        715                 720                 725

ttt gag aag aac tgg gat ttg gac agt aga gag ctt gtt cag gaa atc      2261
Phe Glu Lys Asn Trp Asp Leu Asp Ser Arg Glu Leu Val Gln Glu Ile
    730                 735                 740

aag aac ttg cct aac tta cca tca acg act cca agt ctc ctt gag ctc      2309
Lys Asn Leu Pro Asn Leu Pro Ser Thr Thr Pro Ser Leu Leu Glu Leu
745                 750                 755                 760

atc tct ttc atg tct gat aag gat cta tca gaa atc tat ccg aac ttt      2357
Ile Ser Phe Met Ser Asp Lys Asp Leu Ser Glu Ile Tyr Pro Asn Phe
                765                 770                 775

tgg act gct ctc agg att gca ctc acc ttg cca gtc act gtg gct caa      2405
Trp Thr Ala Leu Arg Ile Ala Leu Thr Leu Pro Val Thr Val Ala Gln
            780                 785                 790

gca gag agg agc ttt tca aaa cta aaa ttg atc aag tcg tac ctg agg      2453
Ala Glu Arg Ser Phe Ser Lys Leu Lys Leu Ile Lys Ser Tyr Leu Arg
        795                 800                 805

tca aca atg tca cag gag cga ctc act aac ctt gcc gtt gtt agc atc      2501
Ser Thr Met Ser Gln Glu Arg Leu Thr Asn Leu Ala Val Val Ser Ile
    810                 815                 820

aat cac tca gta ggg gag cag ata tca tat gat gat gtt att gac gag      2549
Asn His Ser Val Gly Glu Gln Ile Ser Tyr Asp Asp Val Ile Asp Glu
825                 830                 835                 840

ttt gca tca aga aag gct agg aag gtt agg ttt tag ttggtgtttt           2595
Phe Ala Ser Arg Lys Ala Arg Lys Val Arg Phe
                845                 850

ctgttattgt attggtgctg cagttatatt tattttagcg tgtcatttgt gtgataaaag   2655

gtttgtgctt tataatattt attttatatt atttattcaa tattgagttt gattcaatat   2715

tttcttagct aactgtattt ttgccatgct                                    2745


<210> SEQ ID NO 17
<211> LENGTH: 851
<212> TYPE: PRT
<213> ORGANISM: Oryzias latipes

<400> SEQUENCE: 17

Met Glu Lys Lys Arg Ser Lys Pro Ser Gly Ala Gln Phe Arg Lys Lys
1               5                   10                  15

Arg Lys Glu Glu Glu Glu Lys Arg Asp Lys Glu Lys Gly Ala Leu Leu
            20                  25                  30

Arg Tyr Phe Gly Ser Ser Thr Thr Ala Gln Asp Glu Thr Ser Thr Ser
        35                  40                  45

Leu Pro Ala Ile Ser Ser Ala Thr Val Thr Val Ser Pro Pro Gln Asp
    50                  55                  60

Glu Leu Pro Ser Thr Ser Ser Ala Thr His Val Val Pro Gln Leu Leu
65                  70                  75                  80

Pro Glu Gln Ser Phe Asp Ser Glu Ala Glu Asp Val Val Pro Ser Thr
                85                  90                  95
```

```
Ser Thr Gln Leu Glu Thr Ser Glu Met Pro Gly Asp Glu Thr Pro Leu
            100                 105                 110

Thr Pro Thr Ala Glu Asp Gln Pro Leu Pro Thr Asp Pro Ala Lys Trp
        115                 120                 125

Pro Ser Pro Leu Thr Asp Arg Ile Arg Met Glu Leu Val Arg Arg Gly
    130                 135                 140

Pro Ser Ser Ile Pro Pro Asp Phe Val Phe Pro Arg Asn Asp Ser Asp
145                 150                 155                 160

Gly Arg Ser Cys His His His Tyr Phe Arg Lys Thr Leu Val Ser Gly
                165                 170                 175

Glu Lys Ile Ala Arg Thr Trp Leu Met Tyr Ser Lys Val Lys Asn Ser
            180                 185                 190

Leu Phe Cys Phe Cys Cys Lys Leu Phe Ser Asn Lys Asn Ile Asn Leu
        195                 200                 205

Thr Thr Ser Gly Thr Ala Asn Trp Lys His Ala Ser Thr Tyr Leu Thr
    210                 215                 220

Ala His Glu Lys Ser Pro Glu His Leu Asn Cys Met Lys Ala Trp Lys
225                 230                 235                 240

Glu Leu Ser Gly Arg Ile Arg Ser Gly Lys Thr Ile Asp Lys Gln Glu
                245                 250                 255

Met Ala Leu Leu Glu Glu Glu Arg Val Arg Trp Arg Ala Val Leu Thr
            260                 265                 270

Arg Leu Ile Ala Ile Val Gln Ser Leu Ala Val Arg Asn Leu Ala Leu
        275                 280                 285

Arg Gly His Thr Glu Thr Leu Phe Thr Ser Ser Asn Gly Asn Phe Leu
    290                 295                 300

Lys Glu Val Glu Leu Met Ala Arg Phe Asp Pro Ile Met Lys Asp His
305                 310                 315                 320

Leu Asn Arg Val Leu Arg Gly Thr Ala Ser His Asn Ser Tyr Ile Gly
                325                 330                 335

His His Val Gln Asn Glu Leu Ile Asp Leu Leu Ser Ser Lys Ile Leu
            340                 345                 350

Ser Ala Ile Val Asp Asp Ile Lys Lys Ala Lys Tyr Phe Ser Ile Ile
        355                 360                 365

Leu Asp Cys Thr Leu Asp Ile Ser His Thr Glu Gln Leu Ser Val Ile
    370                 375                 380

Ile Arg Val Val Ser Leu Met Glu Lys Pro Gln Ile Arg Glu His Phe
385                 390                 395                 400

Met Gly Phe Leu Glu Ala Glu Glu Ser Thr Gly Gln His Leu Ala Ser
                405                 410                 415

Met Ile Leu Asn Arg Leu Glu Glu Leu Gly Ile Ser Phe Glu Asp Cys
            420                 425                 430

Arg Gly Gln Ser Tyr Asp Asn Gly Ala Asn Met Lys Gly Lys Asn Lys
        435                 440                 445

Gly Val Gln Ala Arg Leu Leu Glu Lys Asn Pro Arg Ala Leu Phe Leu
    450                 455                 460

Pro Cys Gly Ala His Thr Leu Asn Leu Val Val Cys Asp Ala Ala Lys
465                 470                 475                 480

Arg Ser Val Asp Ala Met Ser Tyr Phe Gly Val Leu Gln Lys Leu Tyr
                485                 490                 495

Thr Leu Phe Ser Ala Ser Ala Gln Arg Trp Ala Ile Leu Lys Ser Gln
            500                 505                 510

Val Ser Ile Thr Leu Lys Ser Trp Thr Glu Thr Arg Trp Glu Ser Lys
```

```
        515                 520                 525

Ile Lys Ser Ile Glu Pro Met Arg Tyr Gln Gly Ala Ala Val Arg Glu
    530                 535                 540

Ala Leu Ile Glu Val Arg Asp Lys Thr Lys Asp Pro Val Ile Lys Ala
545                 550                 555                 560

Glu Ala Gln Ser Leu Ser Glu Glu Val Gly Ser Tyr Arg Phe Asn Ile
                565                 570                 575

Cys Thr Val Val Trp His Asp Ile Leu Ser Thr Ile Lys His Val Ser
            580                 585                 590

Lys Leu Met Gln Ser Pro Asn Met His Val Asp Leu Ala Val Ser Leu
        595                 600                 605

Leu Lys Lys Thr Glu Gln Ser Leu Gln Ser Tyr Arg Ala Asn Gly Phe
    610                 615                 620

Val Asn Ala Gln Met Ala Ala Lys Glu Met Cys Lys Glu Met Asn Val
625                 630                 635                 640

Glu Ala Ile Leu Lys Gln Lys Arg Ile Arg Ser Thr Lys Cys Gln Phe
                645                 650                 655

Ser Tyr Glu Ser His Asp Glu Pro Phe Ser Asp Ala Leu Lys Lys Leu
            660                 665                 670

Glu Val Glu Phe Phe Asn Val Val Val Asp Glu Ala Leu Ser Ala Ile
        675                 680                 685

Ala Glu Arg Phe Ser Thr Leu Glu Val Val Gln Asn Arg Phe Gly Val
    690                 695                 700

Leu Thr Asn Phe Pro Ser Leu Gly Asp Glu Glu Leu Thr Glu Gln Cys
705                 710                 715                 720

Glu Ala Leu Gly Asn Ile Leu His Phe Glu Lys Asn Trp Asp Leu Asp
                725                 730                 735

Ser Arg Glu Leu Val Gln Glu Ile Lys Asn Leu Pro Asn Leu Pro Ser
            740                 745                 750

Thr Thr Pro Ser Leu Leu Glu Leu Ile Ser Phe Met Ser Asp Lys Asp
        755                 760                 765

Leu Ser Glu Ile Tyr Pro Asn Phe Trp Thr Ala Leu Arg Ile Ala Leu
    770                 775                 780

Thr Leu Pro Val Thr Val Ala Gln Ala Glu Arg Ser Phe Ser Lys Leu
785                 790                 795                 800

Lys Leu Ile Lys Ser Tyr Leu Arg Ser Thr Met Ser Gln Glu Arg Leu
                805                 810                 815

Thr Asn Leu Ala Val Val Ser Ile Asn His Ser Val Gly Glu Gln Ile
            820                 825                 830

Ser Tyr Asp Asp Val Ile Asp Glu Phe Ala Ser Arg Lys Ala Arg Lys
        835                 840                 845

Val Arg Phe
    850
```

PROTEIN PRODUCTION METHOD

This application is a Continuation of U.S. application Ser. No. 14/689,782, filed Apr. 17, 2015 (now allowed); which is a Continuation of U.S. application Ser. No. 12/813,920 filed Jun. 11, 2010 (now U.S. Pat. No. 9,034,649); which claims the benefit of U.S. Provisional Application No. 61/186,138, filed Jun. 11, 2009; and which claims priority to Japanese Patent Application No. 2009-140626, filed Jun. 11, 2009; the contents of all of which are incorporated herein by reference in their entireties.

BACKGROUND OF THE INVENTION

1. Field of the Invention

This invention relates to a method for producing a protein of interest, comprising introducing a protein expression vector which comprises a gene fragment comprising a DNA encoding a protein of interest and a selectable marker gene and transposon sequences at both terminals of the gene fragment, into a suspension mammalian cell, integrating the gene fragment inserted between a pair of the transposon sequences into a chromosome of the mammalian cell to obtain a mammalian cell capable of expressing the protein of interest; and suspension-culturing the mammalian cell; and a suspension mammalian cell capable of expressing the protein of interest.

2. Brief Description of the Background Art

Production of exogeneous proteins by recombinant DNA techniques is used in various industries such as pharmaceutical industry and food industry. In most cases, production of recombinant proteins is carried out by introducing an expression vector comprising a nucleotide sequence encoding a protein of interest into a host, such as *Escherichia coli*, yeast, insect cell, plant cell, and animal cell, selecting a transformant in which the expression vector is integrated into the chromosome, and further culturing the cell line under appropriate culture conditions.

However, in order to develop a host which can produce an exogeneous protein efficiently, it is necessary to select a host cell having good productivity for each protein of interest, so that a further technical innovation is desired on the exogeneous protein production techniques for individual host.

In the bacteria systems, such as *Escherichia coli*, and yeast systems, different from animal cells, post-translational modifications, such as sugar chain modification, are difficult to attain in many cases and thus cause a problem in producing a protein having its activity.

Since the produced protein is subject to a post-translational modification such as phosphrylation and addition of sugar chains in the insect system, this system has a merit that the protein having its original physiological activity can be expressed. However, since the sugar chain structure of the secreted protein is different from that of mammalians-derived cells, antigenicity and the like become a problem when the protein is applied to pharmaceutical use.

In addition, since a recombinant virus is used in the insect cell system when an exogeneous gene is introduced, there is a problem that its inactivation and containment of the virus are required from the viewpoint of safety.

In the animal cell system, post-translational modifications, such as phosphorylation, sugar chain addition, and folding, can be conducted to proteins derived from higher animals including human, in more similar manner to those produced in the living body. Such accurate post-translational modifications are necessary for recreating the physiological activity originally possessed by a protein in its recombinant protein, and a protein production system in which a mammalian cell is used as a host is usually applied to pharmaceutical products and the like that requires such physiological activity.

However, a protein expression system in which a mammalian cell is used as the host is generally low in productivity, and also causes a problem of the stability of introduced genes in many cases. Improvement of productivity of a protein using a mammalian culture cell as a host is not only very important in producing medicaments for treatment, diagnostic agents and the like, but also greatly contributes to research and development of them. Thus, it is urgent to develop a gene expression system which easily makes it possible to obtain a cell line of a high productivity using a mammalian culture cell, particularly Chinese hamster ovary cell (CHO cell), as the host.

A transposon is a transposable genetic element which can transfer from one locus to other locus on the chromosome. A transposon is a strong tool for the study on molecular biology and genetics and used for a purpose, such as mutagenesis, gene trapping, and preparation of transgenic individuals, in insects or nematode (e.g., *Drosophila melanogaster* or *Caenorhabditis elegans*) and plants. However, development of such a technique has been delayed for vertebral animals including mammalian cells.

In recent years, however, transposons which have activities also in vertebral animals have been reported, and some of them were shown to have an activity in mammalian cells, such as cell derived from mouse and human. Typical examples include transposons Tol1 (Patent Reference 1) and Tol2 (Non-patent Reference 1) cloned from a medaka (killifish), Sleeping Beauty reconstructed from a non-autonomous transposon existed in *Onchorhynchus* fish genome (Non-patent Reference 2), an artificial transposon Frog prince (Non-patent Reference 3) which is derived from frog and a transposon piggyBac (Non-patent Reference 4) which is derived from insect.

These DNA transposons have been used for mutagenesis, gene trapping, preparation of transgenic individuals, expression of drug-resistant proteins, and the like, as a gene transfer tool for bringing a new phenotype in a genome of a mammalian cell (Non-patent References 5 to 12).

In the case of insects, a method in which an exogeneous gene is introduced into silkworm chromosome using the transposon piggyBac derived from a Lepidoptera insect to express the protein encoded by said exogeneous gene was studied, and a protein production method using the above techniques has been disclosed (Patent Reference 2).

However, since the expressed protein of interest is not sufficient in expression level and is produced in the whole body of silkworm, it causes an economical problem due to the necessity of an advanced purification technique for recovering the expressed exogeneous protein in a highly purified form from the body fluid including a large amount of contaminated proteins.

In addition, an example in which a protein relating to G418 resistance is expressed in a mammalian cell using the medaka-derived transposon Tol2 (Non-patent Reference 12) is known.

CITATION LIST

Patent Literature

[Patent Literature 1] WO2008/072540
[Patent Literature 2] Japanese Published Unexamined Patent Application No. 2001-532188

Non Patent Literature

[Non Patent Literature 1] *Nature* 383, 30 (1996)
[Non Patent Literature 2] *Cell* 91, 501-510 (1997)
[Non Patent Literature 3] *Nucleic Acids Res,* 31, 6873-6881 (2003)
[Non Patent Literature 4] *Insect Mol. Biol.* 5, 141-151 (1996)
[Non Patent Literature 5] *Genetics.* 166, 895-899 (2004)
[Non Patent Literature 6] *PLoS Genet,* 2, e169 (2006)
[Non Patent Literature 7] *Proc. Natl. Acad. Sci. USA* 95, 10769-10773 (1998)
[Non Patent Literature 8] *Proc. Natl. Acad. Sci. USA* 98:6759-6764 (2001)
[Non Patent Literature 9] *Nature* 436, 221-226 (2005)
[Non Patent Literature 10] *Nucleic Acids Res.,* 31, 6873-6881 (2003)
[Non Patent Literature 11] *Nucleic Acids Res.,* 35, e87 (2007)
[Non Patent Literature 12] *Proc Natl. Acad. Sci. USA,* 103, 15008-15013 (2006)

SUMMARY OF THE INVENTION

In order to produce and analyze a protein of interest, it is necessary to select a cell line which stably and highly expresses a protein of interest, using a mammalian-derived culture cell, but preparation and culture of the cell that produces the protein of interest require considerable labor and time.

In addition, though it is known that a protein of interest is expressed in a mammalian cell using a transposon sequence, preparation of a cell which can highly express a protein of interest and thus can be used as a protein production system by using a transposon sequence; preparation method of a mammalian cell which can highly produce a protein of interest by using a transposon sequence; and a production method of a protein using the cell are not known.

As described in the above, the expression of a protein of interest in a large amount by establishing a protein production system which can highly produce a protein of interest using a mammalian culture cell efficiently and within a short period has been required. Thus, the objects of the invention are to provide a cell capable of highly expressing a protein of interest which can be efficiently established, and a method for producing the protein of interest using the cell.

Solution to Problems

To solve the above-mentioned problems, the present inventors have conducted intensive studies and found as a result that a mammalian cell capable of highly expressing a protein of interest can be efficiently prepared by introducing a protein expression vector which comprises a gene fragment comprising a DNA encoding the protein of interest and a selectable marker gene and transposon sequences at both terminals of the gene fragment, into a suspension mammalian cell; and integrating the gene fragment inserted between a pair (two) of the transposon sequences into a chromosome of the mammalian cell. In addition, it was found that the protein of interest can be produced efficiently by using the cell, and thereby the invention was accomplished.

According to the protein production method of the invention, a protein of interest can be efficiently produced by the use of a mammalian cell. In addition, the cell of the invention can be used as a protein production cell for producing a recombinant protein with a high efficiency.

DETAILED DESCRIPTION OF THE INVENTION

Figure 1:
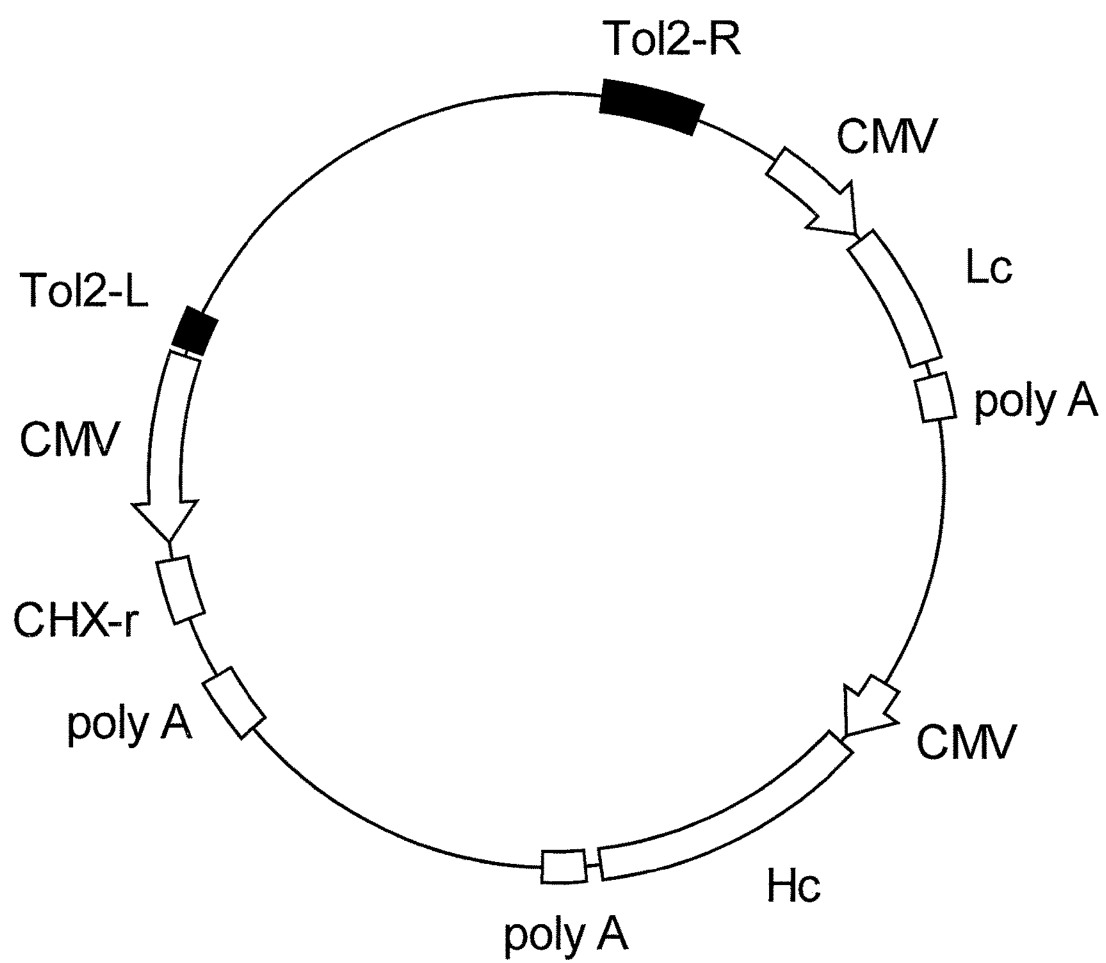
FIG. 1 shows a schematic illustration of a transposon vector for expressing an anti-human influenza M2 antibody. Tol2-L represents a left end Tol2 transposon (SEQ ID NO:2), Tol2-R represents a right end Tol2 transposon (SEQ ID NO:3), CMV represents a CMV promoter, poly A represents a polyadenylation site, Hc represents a human antibody H chain cDNA, Lc represents a human antibody L chain cDNA, and CHX-r represents a cycloheximide resistance gene.

Specifically, the invention relates to the following 1 to 31:

1. A method for producing a protein of interest, comprising introducing a protein expression vector which comprises a gene fragment comprising a DNA encoding a protein of interest and a selectable marker gene and transposon sequences at both terminals of the gene fragment, into a suspension mammalian cell; integrating the gene fragment inserted between a pair of the transposon sequences into a chromosome of the mammalian cell to obtain a mammalian cell capable of expressing the protein of interest; and suspension-culturing the mammalian cell;

2. A method for producing a protein of interest, comprising the following steps (A) to (C):

(A) a step of simultaneously introducing the following expression vectors (a) and (b) into a suspension mammalian cell:

(a) an expression vector which comprises a gene fragment comprising a DNA encoding a protein of interest and transposon sequences at both terminals of the gene fragment, (b) an expression vector which comprises a DNA encoding a transposase which recognizes the transposon sequences and has activity of transferring a gene fragment inserted between a pair of the transposon sequences into a chromosome, (B) a step of expressing transiently the transposase from the expression vector introduced in the step (A) to integrate the gene fragment inserted between a pair of the transposon sequences into a chromosome of the mammalian cell to obtain a suspension mammalian cell capable of expressing the protein of interest, and (C) a step of suspension-culturing the suspension mammalian cell capable of expressing the protein of interest obtained in the step (B) to produce the protein of interest;

3. A method for obtaining a suspension mammalian cell capable of expressing a protein of interest, comprising introducing a protein expression vector which comprises a gene fragment comprising a DNA encoding a protein of interest and a selectable marker gene and transposon sequences at both terminals of the gene fragment into a suspension mammalian cell; and integrating the gene fragment inserted between a pair of the transposon sequences, into a chromosome of the mammalian cell;

4. The method described in any one of the aforementioned items 1 to 3, wherein the suspension mammalian cell is a cell capable of surviving and proliferating in a serum-free medium;

5. The method described in any one of the aforementioned items 1 to 4, wherein the suspension mammalian cell is at least one selected from a suspension CHO cell in which a CHO cell is adapted to suspension culture, a PER.C6 cell, a rat myeloma cell YB2/3HL.P2.G11.16Ag.20 (or also called YB2/0) and a suspension mouse myeloma cell NS0 adapted to suspension culture;

6. The method described in the aforementioned item 5, wherein the CHO cell is at least one selected from CHO-K1, CHO-K1SV, DUKXB11, CHO/DG44, Pro-3 and CHO-S;

7. The method described in any one of the aforementioned items 1 to 6, wherein the selectable marker gene is a cycloheximide resistance gene;

8. The method described in the aforementioned item 7, wherein the cycloheximide resistance gene is a gene encoding a mutant of human ribosomal protein L36a;

9. The method described in the aforementioned item 8, wherein the mutant is a mutant in which proline at position 54 of the human ribosomal protein L36a is substituted with other amino acid;

10. The method described in the aforementioned item 9, wherein the other amino acid is glutamine;

11. The method described in any one of the aforementioned items 1 to 10, wherein a pair of the transposon sequences are nucleotide sequences derived from a pair of DNA-type transposons which function in a mammalian cell;

12. The method described in the aforementioned item 11, wherein the nucleotide sequences derived from a pair of DNA type transposons are nucleotide sequences derived from a pair of Tol1 transposons or nucleotide sequences derived from a pair of Tol2 transposons;

13. The method described in the aforementioned item 12, wherein the nucleotide sequences derived from a pair of Tol2 transposons are a nucleotide sequence comprising the nucleotide sequence shown in SEQ ID NO:2 and the nucleotide sequence shown in SEQ ID NO:3;

14. The method described in the aforementioned item 12, wherein the nucleotide sequences derived from a pair of Tol1 transposons are the nucleotide sequence shown in SEQ ID NO:14 and the nucleotide sequence shown in SEQ ID NO:15;

15. A suspension mammalian cell capable of producing a protein of interest, into which a protein expression vector comprising a gene fragment comprising a DNA encoding a protein of interest and a selectable marker gene and transposon sequences at both terminals of the gene fragment is introduced, to integrate the gene fragment inserted between a pair of the transposon sequences into a chromosome;

16. A suspension mammalian cell capable of producing a protein of interest, into which an expression vector (a) comprising a gene fragment comprising a DNA encoding a protein of interest and a selectable marker gene and transposon sequences at both terminals of the gene fragment, and an expression vector (b) comprising a DNA encoding a transposase (a transferase) which recognizes the transposon sequences and has activity of transferring the gene fragment inserted between a pair of the transposon sequences into a chromosome to integrate the gene fragment inserted between a pair of the transposon sequences into the chromosome;

17. The cell described in the aforementioned item 15 or 16, wherein the cell is a cell capable of surviving and proliferating in a serum-free medium;

18. The cell described in any one of the aforementioned items 15 to 17, wherein the cell is at least one suspension mammalian cell selected from a suspension CHO cell in which a CHO cell is adapted to suspension culture, a PER.C6 cell, a rat myeloma cell YB2/3HL.P2.G11.16Ag.20 (or also called YB2/0) and a suspension mouse myeloma cell NS0 adapted to suspension culture;

19. The cell described in the aforementioned item 18, wherein the CHO cell is at least one selected from CHO-K1, CHO-K1SV, DUKXB11, CHO/DG44, Pro-3 and CHO-S;

20. The cell described in any one of the aforementioned items 15 to 19, wherein the selectable marker gene is a cycloheximide resistance gene;

21. The cell described in the aforementioned item 20, wherein the cycloheximide resistance gene is a gene encoding a mutant of human ribosomal protein L36a;

22. The cell described in the aforementioned item 21, wherein the mutant is a mutant in which proline at position 54 of the human ribosomal protein L36a is substituted with other amino acid;

23. The cell described in the aforementioned item 22, wherein the other amino acid is glutamine;

24. The cell described in any one of the aforementioned items 15 to 23, wherein a pair of the transposon sequences are nucleotide sequences derived from a pair of DNA-type transposons which function in a mammalian cell;

25. The cell described in the aforementioned item 24, wherein the nucleotide sequences derived from a pair of the DNA-type transposons are nucleotide sequences derived from a pair of Tol1 transposons or nucleotide sequences derived from a pair of Tol2 transposons;

26. The cell described in the aforementioned item 25, wherein the nucleotide sequences derived from a pair of the Tol2 transposons are the nucleotide sequence shown in SEQ ID NO:2 and the nucleotide sequence shown in SEQ ID NO:3;

27. The cell described in the aforementioned item 25, wherein the nucleotide sequences derived from a pair of the Tol1 transposons are the nucleotide sequence shown in SEQ ID NO:14 and the nucleotide sequence shown in SEQ ID NO:15;

28. A protein expression vector, comprising a gene fragment comprising a DNA encoding a protein of interest and a selectable marker gene, and a pair of transposon sequences at both terminals of the gene fragment;

29. The protein expression vector described in the aforementioned item 28, wherein a pair of the transposon sequences are nucleotide sequences derived from a pair of Tol1 transposons or nucleotide sequences derived from a pair of Tol2 transposons.

30. The protein expression vector described in the aforementioned item 29, wherein the nucleotide sequences derived from a pair of the Tol2 transposons are the nucleotide sequence shown in SEQ ID NO:2 and the nucleotide sequence shown in SEQ ID NO:3; and 31. The protein expression vector described in the aforementioned item 29, wherein the nucleotide sequences derived from a pair of the Tol1 transposons are the nucleotide sequence shown in SEQ ID NO:14 and the nucleotide sequence shown in SEQ ID NO:15.

This invention relates to a method for producing a protein of interest, comprising introducing a protein expression vector comprising a gene fragment comprising a DNA encoding a protein of interest and a selectable marker gene and transposon sequences at both terminals of the gene fragment, into a suspension mammalian cell; integrating the gene fragment inserted between a pair (two) of the transposon sequences, into a chromosome of the mammalian cell to obtain a mammalian cell capable of expressing said protein of interest; and suspension-culturing the mammalian cell.

Examples of the method for producing a protein of interest of the present invention include a method, comprising the following steps (A) to (C):

(A) a step of simultaneously introducing the following expression vectors (a) and (b) into a suspension mammalian cell:

(a) an expression vector which comprises a gene fragment comprising a DNA encoding a protein of interest and transposon sequences at both terminals of the gene fragment, (b) an expression vector which comprises a DNA encoding a transposase which recognizes the transposon sequences and has activity of transferring a gene fragment inserted between a pair of the transposon sequences into a chromosome, (B) a step of expressing transiently the transposase transiently from the expression vector introduced in the step (A) to integrate the gene fragment inserted between a pair of the transposon sequences into a chromosome of the mammalian cell to obtain a suspension mammalian cell capable of expressing the protein of interest, and (C) a step of suspension-culturing the suspension mammalian cell capable of expressing the protein of interest obtained in the step (B) to produce the protein of interest.

In addition, the present invention relates to a suspension mammalian cell capable of producing a protein of interest, into which a protein expression vector comprising a gene fragment comprising a DNA encoding a protein of interest and a selectable marker gene and transposon sequences at both terminals of the gene fragment is introduced, to integrate the gene fragment inserted between a pair of the transposon sequences into a chromosome.

Furthermore, the present invention relates to a suspension mammalian cell capable of producing a protein of interest, into which an expression vector (a) comprising a gene fragment comprising a DNA encoding a protein of interest and a selectable marker gene and transposon sequences at both terminals of the gene fragment, and an expression vector (b) comprising a DNA encoding a transposase (a transferase) which recognizes the transposon sequences and has activity of transferring the gene fragment inserted between a pair of the transposon sequences into a chromosome to integrate the gene fragment inserted between a pair of the transposon sequences into the chromosome.

The term "transposon" in the present specification is a transposable genetic element and means a gene unit which moves on a chromosome or from a chromosome to other chromosome (transposition) while keeping a certain structure.

The transposon comprises a gene unit of a repeating transposon sequences (also called inverted repeat sequence (IR sequence) or terminal inverted repeat sequence (TIR sequence)) which positions in the same direction or the reverse direction at both terminals of the gene unit and a nucleotide sequence encoding a transposase which recognizes the transposon sequence to transfer a gene existing between the transposon sequences.

The transposase translated from the transposon can transfer a DNA by recognizing transposon sequences of both terminals of the transposon, cutting out the DNA fragment inserted between a pair of the transposon sequences and inserting the fragment into the site to be transferred.

The term "transposon sequence" in the present specification means the nucleotide sequence of a transposon recognized by a transposase and has the same meaning as the IR sequence or TIR sequence. A DNA comprising the nucleotide sequence may comprise an imperfect repeating moiety as long as it can be transferred (inserted into other position in the genome) by the activity of a transposase, and comprise a transposon sequence specific to the transposase.

As the transposon sequence to be used in the invention, a nucleotide sequence derived from a DNA-type transposon is preferable, and a nucleotide sequence derived from a pair of natural or artificial DNA-type transposons, which can be recognized by a transposase and be transposed in mammalian cells, is more preferable.

Examples of the nucleotide sequence derived from a DNA-type transposon include the nucleotide sequences derived from the medaka fish-derived Tol1 transposon and Tol2 transposon, the Sleeping Beauty reconstructed from a non-autonomous transposon existed in an *Onchorhynchus* fish genome, the frog-derived artificial transposon Frog prince and the insect-derived transposon PiggyBac.

Particularly, among them, the nucleotide sequences derived from the medaka fish-derived Tol2 transposon comprising the nucleotide sequence shown in SEQ ID NO:6 and the medaka fish-derived Tol2 transposon comprising the nucleotide sequence shown in SEQ ID NO:13 are preferable.

Examples of the nucleotide sequence derived from a pair of Tol2 transposons include the nucleotide sequence at positions 1 to 2229 and the nucleotide sequence at positions 4148 to 4682 in the Tol2 transposon nucleotide sequence shown in SEQ ID NO:6 of Sequence Listing.

As the nucleotide sequence derived from a pair of Tol2 transposons, the nucleotide sequence at positions 1 to 200 (SEQ ID NO:2) (hereinafter referred to as "Tol2-L sequence") and the nucleotide sequence at positions 2285 to 2788 (SEQ ID NO:3) (hereinafter referred to as "Tol2-R sequence") in the Tol2 transposon nucleotide sequence shown in SEQ ID NO:1 of Sequence Listing are more preferable.

Examples of the nucleotide sequence derived from a pair of Tol1 transposons include the nucleotide sequence comprising a nucleotide sequence at positions 1 to 157 and the nucleotide sequence at positions the 1748 to 1855 in the Tol1 transposon nucleotide sequence shown in SEQ ID NO:13 of Sequence Listing.

As the nucleotide sequence derived from a pair of Tol1 transposons, the nucleotide sequence at positions 1 to 200 (SEQ ID NO:14) (hereinafter referred to as "Tol1-L sequence") and the nucleotide sequence at positions 1351 to 1855 (SEQ ID NO:15) (hereinafter referred to as "Tol1-R sequence") in the Tol2 transposon nucleotide sequence shown in SEQ ID NO:1 of Sequence Listing are more preferable.

Examples of the transposon sequence to be used in the invention include transposon sequences of which transfer reactions are controlled by using a partial sequence of a transposon sequence derived from the above-mentioned transposon, by adjusting the length of the nucleotide sequence and by modifying the nucleotide sequence due to addition, deletion or substitution.

Regarding the control of the transfer reaction of a transposon, the transfer reaction can be accelerated or suppressed by accelerating or suppressing recognition of the transposon sequence by a transposase, respectively.

The term "transposase" in the present specification means an enzyme which recognizes nucleotide sequences having transposon sequences and transfers a DNA existing between the nucleotide sequences into a chromosome or from the chromosome to other chromosome.

Examples of the transposase include the Tol1 and Tol2 which are derived from medaka fish, the Sleeping Beauty reconstructed from a non-autonomous transposon existed in an *Onchorhynchus* fish genome, the artificial transposon Frog prince which is derived from frog and the transposon PiggyBac which is derived from insect.

As the transposase, a native enzyme may be used, and any transposase in which a part of its amino acids are substituted, deleted, inserted and/or added may be used as long as the same transfer activity as the transposase is maintained. By controlling the enzyme activity of the transposase, the transfer reaction of the DNA existing between the transposon sequences can be controlled.

In order to analyze whether or not it possesses a transfer activity similar to that of transposase, it can be measured by the 2-components analyzing system disclosed in Japanese Published Unexamined Patent Application No. 235575/2003.

Illustratively, whether or not a non-automatic Tol2 element can be transferred and inserted into a mammalian cell chromosome by the activity of a transposase can be analyzed by separately using a plasmid comprising a Tol2 transposase-deleted Tol2 transposon (Tol2-derived non-autonomous transposon) and a plasmid comprising Tol2 transposase.

The term "non-autonomous transposon" in the present specification means a transposon which is lost a transposase existed inside the transposon and cannot therefore perform its autonomous transfer. The non-autonomous transposon can transfer the DNA inserted between transposon sequences of the non-autonomous transposon into the host cell chromosome, by allowing a transposase protein, an mRNA encoding the transposase protein or a DNA encoding the transposase protein to simultaneously present in the cell.

The transposase gene means a gene encoding a transposase. In order to improve its expression efficiency in a mammalian cell, a sequence which adjusts a space between the Kozak's consensus sequence (Kozak M., *Nucleic Acids Res.,* 12, 857-872 (1984)) or a ribosome binding sequence, Shine-Dalgarno sequence and the initiation codon, to an appropriate distance (e.g., from 6 to 18 bases) may be connected to an upstream site of the translation initiation codon ATG of the gene.

According to the method of the invention, in order to integrate a gene fragment comprising a DNA encoding the protein of interest and a selectable marker gene in an expression vector into the chromosome of a host cell, an expression vector which comprises the gene fragment comprising a DNA encoding the protein of interest and a selectable marker gene and transposon sequences at both terminals of the gene fragment is introduced into the host cell, and a transposase is allowed to act upon the transposon sequences comprised in the expression vector which is introduced into the cell.

In order to allow a transposase to act upon the transposon sequences comprised in the expression vector which is introduced into the cell, the transposase may be injected into the cell, or an expression vector comprising a DNA encoding the transposase may be introduced into the host cell together with an expression vector comprising a DNA encoding the protein of interest and a selectable marker gene. In addition, by introducing an RNA encoding a transposase gene into the host cell, the transposase may be expressed in the cell.

The expression vector is not particularly limited. Any expression vector can be used by optionally selecting from the expression vectors known to those skilled in the art, depending on a host cell into which an expression vector comprising a transposase gene is introduced; the use; and the like.

In order that a protein constituted from two or more polypeptides is produced by the method of the invention, the DNA can be integrated into the chromosome of the cell by integrating a DNA encoding the two or more polypeptides into the same or different expression vectors and then introducing the expression vectors into a host cell.

The transposase may be inserted into an expression vector to express together with the protein of interest or may be inserted into a vector different from the expression vector. The transposase may be allowed to act transiently or may be allowed to act continuously, but it is preferably to allow the transposase to act transiently in order to prepare a cell for stable production.

As the method for allowing the transposase to act transiently, examples include a method comprising preparing an expression vector which comprises a DNA encoding the transposase and an expression vector comprising a DNA encoding a protein of interest and then introducing both of the expression plasmids simultaneously into a host cell.

The term "expression vector" in the present specification means an expression vector to be used for introducing a mammalian cell in order to express a protein of interest. The expression vector used in the invention has a structure in which at least a pair of transposon sequences is present at both sides of an expression cassette.

The term "expression cassette" in the present specification means a nucleotide sequence which has a gene expression controlling region necessary for expressing a protein of interest and a sequence encoding the protein of interest. Examples of the gene expression controlling region include an enhancer, a promoter, and a terminator. The expression cassette may contain a selectable marker gene.

Any promoter can be used, so long as it can function in an animal cell. Examples include a promoter of IE (immediate early) gene of cytomegalovirus (CMV), SV40 early promoter, a promoter of retrovirus, a metallothionein promoter, a heat shock promoter, SRa promoter, moloney murine leukemia virus, an enhancer and the like. Also, the enhancer of the IE gene of human CMV can be used together with the promoter.

The "selectable marker gene" means an arbital other marker gene which can be used for distinguishing a cell to which a plasmid vector is introduced from a cell lacking of the vector.

Examples of the selectable marker gene include a drug resistance gene (a neomycin resistance gene, a DHFR gene, a puromycin resistance gene, a blasticidin resistance gene, a hygromycin resistance gene, and a cycloheximide resistance gene (Japanese Published Unexamined Patent Application No. 262879/2002)), fluorescence and bio-luminescence marker genes (such as green fluorescent protein GFP) and the like.

In the invention, preferable selectable marker is a drug resistance gene and particularly preferable selectable marker is a cycloheximide resistance gene. In addition, by carrying out a gene modification of the selectable marker gene, drug resistance performance and luminescence performance of the selectable marker protein can also be modified.

Cycloheximide (hereinafter sometimes referred to as CHX) is a protein synthesis inhibitor, and as examples of the use of the CHX resistance gene as a selectable marker gene, the cases of yeast (Kondo K. *J. Bacteriol.,* 177, 24, 7171-7177 (1995)) and animal cells (Japanese Published Unexamined Patent Application No. 262879/2002) are known.

In the case of the animal cells, it has been found that the resistance to cycloheximide is provided by a transformant which expresses a protein encoded by the nucleotide sequence shown in SEQ ID NO:7 of Sequence Listing in which proline at position 54 in human ribosomal protein subunit L36a encoded by the nucleotide sequence shown in SEQ ID NO:5 of Sequence Listing is substituted with glutamine.

The method for introducing the above-mentioned protein expression vector comprising a transposon sequence, a transposase expressing plasmid vector and RNA is not particularly limited. Examples include calcium phosphate transfection, electroporation, a liposome method, a gene gun method, lipofection and the like.

Examples of the method for directly introducing a transposase in the form of a protein include by microinjection or endocytosis for supplying into a cell. The gene transfer can be carried out by the method described in *Shin Idenshi Kogaku Handbook* (New Genetic Engineering Handbook), edited by Masami Muramatsu and Tadashi Yamamoto, published by Yodo-sha, ISBN 9784897063737.

The host cell may be any mammalian cell as long as it can be subcultured and stably express a protein of interest. Examples of the host cell include PER.C6 cell, human leukemia cell Namalwa cell, monkey cell COS cell, rat myeloma cell YB2/3HL.P2.G11.16Ag.20 (also referred to as YB2/0), mouse myeloma cell NS0, mouse myeloma cell SP2/0-Ag14, Syrian hamster cell BHK, HBT5637 (Japanese Unexamined Patent Application Publication No. 1998-000299), Chinese hamster ovarian cell CHO cell (*Journal of Experimental Medicine,* 108, 945 (1958); *Proc. Natl. Acad. Sci. USA.,* 601275 (1968); *Genetics,* 55, 513 (1968); Chromosoma, 41, 129 (1973); *Methods in Cell Science,* 18, 115 (1996); *Radiation Research,* 148, 260 (1997); *Proc. Natl. Acad. Sci. USA.,* 77, 4216 (1980); *Proc. Natl. Acad. Sci.,* 60, 1275 (1968); *Cell,* 6, 121 (1975); *Molecular Cell Genetics, Appendix I,II* (pp. 883-900)), CHO/DG44, CHO-K1 (ATCC CCL-61), DUKXB11 (ATCC CCL-9096), Pro-5 (ATCC CCL-1781), CHO-S (Life Technologies, Cat #11619), Pro-3 and substrain of CHO cell.

In addition, the above-mentioned host cell can also be used in the protein production method of the invention by modifying it so as to be suitable for the protein production, by modification of chromosomal DNA, introduction of an exogeneous gene, and the like.

Further, in order to control the sugar chain structure bound to a protein of interest to be produced, Lec13 which acquired lectin resistance [*Somatic Cell and Molecular Genetics,* 12, 55 (1986)] and CHO cell from which α1,6-fucosyltransferase gene is deleted (WO2005/35586, WO2002/31140) can also be used as the host cell.

The protein of interest may be any protein so long as it can be expressed by the method of the invention. Specifically, examples include a human serum protein, a peptide hormone, a growth factor, a cytokine, a blood coagulation factor, a fibrinolysis system protein, an antibody and partial fragments of various proteins, and the like.

Preferable examples of the protein of interest include a monoclonal antibody such as a chimeric antibody, a humanized antibody and a human antibody; Fc fusion protein; and albumin-bound protein; and a fragment thereof.

An effector activity of a monoclonal antibody obtained by the method of the present invention can be controlled by various methods. For example, known methods are a method for controlling an amount of fucose (hereinafter, referred to also as "core fucose") which is bound N-acetylglucosamine (GlcNAc) through α-1,6 bond in a reducing end of a complex type N-linked sugar chain which is bound to asparagine (Asn) at position 297 of an Fc region of an antibody (WO2005/035586, WO2002/31140, and WO00/61739), a method for controlling an effector activity of a monoclonal antibody by modifying amino acid group(s) of an Fc region of the antibody, and the like. The effector activity of the monoclonal antibody produced by the method of the present invention can be controlled by using any of the methods.

The "effector activity" means an antibody-dependent activity which is induced via an Fc region of an antibody. As the effector activity, an antibody-dependent cellular cytotoxicity (ADCC activity), a complement-dependent cytotoxicity (CDC activity), an antibody-dependent phagocytosis (ADP activity) by phagocytic cells such as macrophages or dendritic cells, and the like are known.

In addition, by controlling a content of core fucose of a complex type N-linked sugar chain of Fc region of a monoclonal antibody, an effector activity of the antibody can be increased or decreased.

As a method for lowering a content of fucose which is bound to a complex type N-linked sugar chain bound to Fc of the antibody, an antibody to which fucose is not bound can be obtained by the expression of an antibody using a CHO cell which is deficient in a gene encoding α1,6-fucosyltransferase. The antibody to which fucose is not bound has a high ADCC activity.

On the other hand, as a method for increasing a content of fucose which is bound to a complex type N-linked sugar chain bound to Fc of an antibody, an antibody to which fucose is bound can be obtained by the expression of an antibody using a host cell into which a gene encoding α1,6-fucosyltransferase is introduced. The antibody to which fucose is bound has a lower ADCC activity than the antibody to which fucose is not bound.

Further, by modifying amino acid residue(s) in an Fc region of an antibody, the ADCC activity or CDC activity can be increased or decreased. For example, the CDC activity of an antibody can be increased by using the amino acid sequence of the Fc region described in US2007/0148165.

Further, the ADCC activity or CDC activity of an antibody can be increased or decreased by modifying the amino acid as described in U.S. Pat. No. 6,737,056, or 7,297,775 or 7,317,091.

The term "suspension mammalian cell" in the present invention means a cell which does not adhere to a cell culture anchorage coated for facilitating adhesion of culture cells, such as microbeads, a culture container for tissue culture (also referred to as a tissue culture or adhesion culture container and the like) and the like, and can survive and grow by suspending in the culture liquid.

When the cell does not adhere to the cell culture anchorage, it may survive and grow under a state of a single cell in the culture liquid or survive and grow under a state of a cell mass formed by the agglutination of two or more cells.

In addition, as the suspension mammalian cell to be used in the present invention, a cell which can survive and grow in a serum-free medium that does not contain fetal calf serum (hereinafter referred to as FCS) and the like, while suspending in the culture liquid without adhering to the cell culture anchorage, is preferable, and a mammalian cell which can survive and grow while suspending in a protein-free medium that does not contain protein is more preferable.

As the culture container for tissue culture, it may be any culture container such as a flask, a Petri dish and the like, so long as coating for adhesion culture is applied thereto. Specifically, for example, whether or not it is a suspension mammalian cell can be confirmed by the use of commercially available tissue culture flask (manufactured by Greiner), adhesion culture flask (manufactured by Sumitomo Bakelite) and the like.

As the suspension mammalian cell to be used in the present invention, it may be either a cell prepared by further adapting a cell originally having a suspension property to suspension culture or a suspension mammalian cell prepared by adapting an adhesive mammalian cell to suspension culture conditions.

Examples of the cell originally having a suspension property include PER.C6 cell, a rat myeloma cell YB2/3HL.P2.G11.16Ag.20 (or also called YB2/0), CHO-S cell (manufactured by Invitrogen) and the like.

The aforementioned "suspension mammalian cell prepared by adapting an adhesive mammalian cell to suspension culture conditions" can be prepared by the method described in *Mol. Biotechnol.,* 2000, 15(3), 249-57 or by the method shown in the following, and can be prepared by establishing a cell which shows proliferation property and surviving property similar to those before the suspension culture adaptation or superior to those before adapting to suspension culture (*J. Biotechnol.,* 2007, 130(3), 282-90).

The term "similar to those before the suspension culture adaptation" means that survival ratio, proliferation rate (doubling time) and the like of the cell adapted to the suspension culture are substantially the same as those of the cell before adapting suspension culture.

Examples of the method for adapting an adhesive mammalian cell to suspension culture conditions according to the present invention include the following method. The serum content of a serum-containing medium is reduced to 1/10 and sub-culturing is repeated at relatively high concentration of cell. When the mammalian cell comes to be able to survive and proliferate, the serum content is further reduced and the sub-culturing is repeated. By this method, a suspension mammalian cell which can survive and proliferate under serum-free conditions can be prepared.

In addition, a suspension mammalian cell can also be prepared by a method comprising culturing with the addition of an appropriate nonionic surfactant such as Pluronic-F68 or the like in the culture liquid.

Examples of the adhesive mammalian cell which acquires suspension property by adapting to a suspension culture condition include a mouse myeloma cell NS0, a CHO cell and the like.

In the present invention, as a property possessed by the suspension mammalian cell, when $2\times10^5$ cells/ml of the cell is suspension-cultured, the cell concentration after culturing for 3 or 4 days is preferably $5\times10^5$ cells/ml or more, more preferably $8\times10^5$ cells/ml or more, particularly preferably $1\times10^6$ cells/ml or more, most preferably $1.5\times10^6$ cells/ml or more.

In addition, doubling time of the suspension mammalian cell of the present invention is preferably 48 hours or less, more preferably 24 hours or less, particularly preferably 18 hours or less, most preferably 11 hours or less.

Examples of the medium for suspension culturing include commercially available media, such as CD-CHO medium (manufactured by Invitrogen), EX-CELL 325-PF medium (manufactured by SAFC Biosciences), SFM4CHO medium (manufactured by HyClone) and the like. In addition, it can also be obtained by mixing saccharides, amino and the like acids which are necessary for the culturing of mammalian cells.

The suspension mammalian cell can be cultured using a culture container which can be used for suspension culturing under a culture condition capable of suspension culturing. Examples of the culture container include a 96 well plate for cell culture (manufactured by Corning), a T-flask (manufactured by Becton Dickinson), an Erlenmeyer flask (manufactured by Corning) and the like.

Regarding the culture conditions, for example, it can be statically cultured in an atmosphere of 5% $CO_2$ at a culture temperature of 37° C. A shaking culture equipment, such as culturing equipment for suspension culture exclusive use, Wave Bioreactor (manufactured by GE Healthcare Bioscience), can also be used.

Regarding the suspension culture conditions of a suspension mammalian cell using the Wave Bioreactor equipment, the cell can be cultured by the method described on the GE Healthcare Bioscience homepage www.gelifesciences.co.jp/tech-support/manual/pdf/cellcult/wave-03-16.pdf.

In addition to the shaking culture, culturing by a rotation agitation equipment such as a bioreactor, can also be used. Culturing using a bioreactor can be carried out by the method described in *Cytotechnology*, (2006) 52: 199-207, and the like.

In the present invention, when a cell line other than the suspension mammalian cells is used, any cell line can be used so long as it is a mammalian cell line adapted to the suspension culture by the above-mentioned method and is a cell line which can be used in the protein producing method of the present invention.

Purification of the protein of interest produced by the suspension mammalian cell is carried out by separating the protein of interest from impurities other than the protein of interest in a culture liquid or cell homogenate containing the protein of interest. Examples of the separation method include centrifugation, dialysis, ammonium sulfate precipitation, column chromatography, a filter and the like. The separation can be carried out based on the difference in physicochemical properties of the protein of interest and impurities and based on the difference in their affinity for the column carrier.

The method for purifying the protein of interest can be carried out, for example, by the method described in *Protein Experimentation Note* (the first volume)—*Extraction, Separation and Expression of Recombinant Protein* (translation of a textbook written in Japanese) (edited by Masato Okada and Kaori Miyazaki, published by Yodo-sha, ISBN 9784897069180).

The entire contents of the references, such as the scientific documents, patents, patent applications cited herein are incorporated herein by reference to the same degree of those illustratively described, respectively.

The present invention has been described in the foregoing by showing preferred embodiments thereof for the sake of easy understanding. Hereinafter, the present invention is further described specifically based on examples, but the above-mentioned explanations and the following examples are provided merely for the purpose of exemplifications and not provided for the purpose of limiting the invention. Accordingly, the scope of the invention is not limited to the embodiments and examples which are specifically described herein, but is limited by the claims alone.

Various experimental techniques relating to genetic recombination described hereinafter, such as the cloning and the like were carried out in accordance with the genetic engineering techniques described in *Molecular Cloning* 2$^{nd}$ edition edited by J. Sambrook, E. F. Frisch and T. Maniatis, *Current Protocols in Molecular Biology* edited by Frederick M. Ausubel et al, published by Current Protocols, and the like.

By the method for producing the protein of the present invention, a protein of interest can be efficiently produced using a suspension mammalian cell. The cell of the present invention can be used as a protein producing cell for producing a recombinant protein.

EXAMPLES

Example 1

Preparation of Transposon Vector for Expressing Anti-Human Influenza M2 Antibody A plasmid which contains a gene expression cassette for mammalian cells comprising an arbitrary human antibody gene and a drug resistance marker gene inserted between a pair of Tol2 transposon sequences was used as a plasmid vector for protein expression.

Each DNA of the used genes was chemically and artificially synthesized based on a known nucleotide sequence or obtained by preparing primers for its both terminal sequences and then carrying out PCR using an appropriate DNA source as a template. In order to carry out the gene manipulation later, a restriction site for a restriction enzyme was added to the terminal of the primer.

Among the nucleotide sequence of the non-autonomous Tol2 transposone disclosed by Japanese Published Unexamined Patent Application No. 235575/2003 (SEQ ID NO:1), the nucleotide sequence at position 1 to 200 (Tol2-L sequence) (SEQ ID NO:2) and the nucleotide sequence at positions 2285 to 2788 (Tol2-R sequence) (SEQ ID NO:3) were used as the transposon sequences.

Each synthetic DNA fragments comprising a pair of transposon sequences (manufactured by TAKARA BIO INC.) was prepared by the following method. A DNA fragment comprising a nucleotide sequence in which a recognition sequence of a restriction enzyme NruI was attached to both of the 5'-terminal and 3'-terminal of the Tol2-R sequence was prepared. Then, a DNA fragment comprising a nucleotide sequence in which a recognition sequence of a restriction enzyme FseI was attached to the 5'-terminal of the Tol2-L sequence and a restriction enzyme AscI was attached to the 3'-terminal thereof was prepared.

Next, the thus prepared DNA fragments comprising Tol2-R sequence and Tol2-L sequence were inserted into an expression vector N5LG1-M2-Z3 vector (WO2006/061723) comprising a nucleotide sequence encoding an amino acid sequence of anti-human influenza M2 antibody Z3G1.

The N5LG1-M2-Z3 vector (WO2006/061723) into which a nucleotide sequence (SEQ ID NO:8) encoding the H chain of the anti-human influenza M2 antibody Z3G1 (ATCC Deposit No. PTA-5968: deposited Mar. 13, 2004, American Type Culture Collection, Manassas, Va., USA) and a nucleotide sequence (SEQ ID NO:10 and SEQ ID NO:11) encoding the L chain (SEQ ID NO:9) of the same were inserted under the control of the CMV enhancer/promoter control was used as an antibody gene expression cassette.

The DNA fragment comprising the Tol2-R sequence was inserted into the restriction enzyme NruI site of the N5LG1-M2-Z3 vector, at the 5'-terminal side of a gene fragment comprising the antibody gene expression cassette and a resistance marker gene. Then, the DNA fragment comprising the Tol2-L sequence was inserted into the restriction enzyme FseI and AscI sites at the 3'-terminal side.

In addition, a transposon vector for expressing an anti-human influenza M2 antibody was constructed (FIG. 1) by inserting a cycloheximide resistance gene expression cassette connected with a nucleotide sequence (SEQ ID NO:5) encoding a resistance gene for cycloheximide (a gene in which proline at position 54 of the human ribosomal protein L36a was substituted with glutamine) into the FseI recognition site of the N5LG1-M2-Z3 vector connected with the Tol2 transposon sequence, under the control of the CMV enhancer/promoter.

Figure 2:
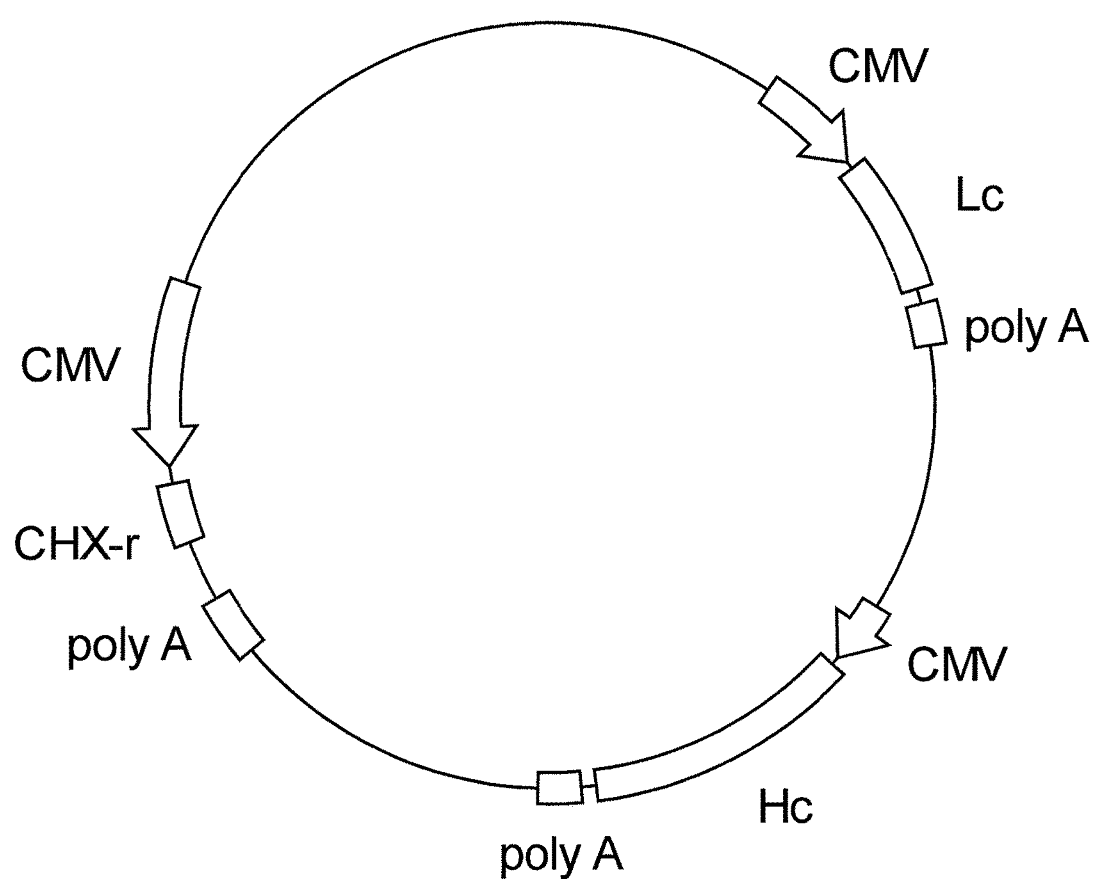
FIG. 2 shows a schematic illustration of an anti-human influenza M2 antibody expression vector. CMV represents a CMV promoter, poly A represents a polyadenylation site, Hc represents a human antibody H chain cDNA, Lc represents a human antibody L chain cDNA and CHX-r represents a cycloheximide resistance gene.

On the other hand, a vector containing no transposon sequences was named anti-human influenza M2 antibody expression vector and used as the control vector (FIG. 2).

Example 2

Preparation of Transposase Expression Vector

Figure 3:
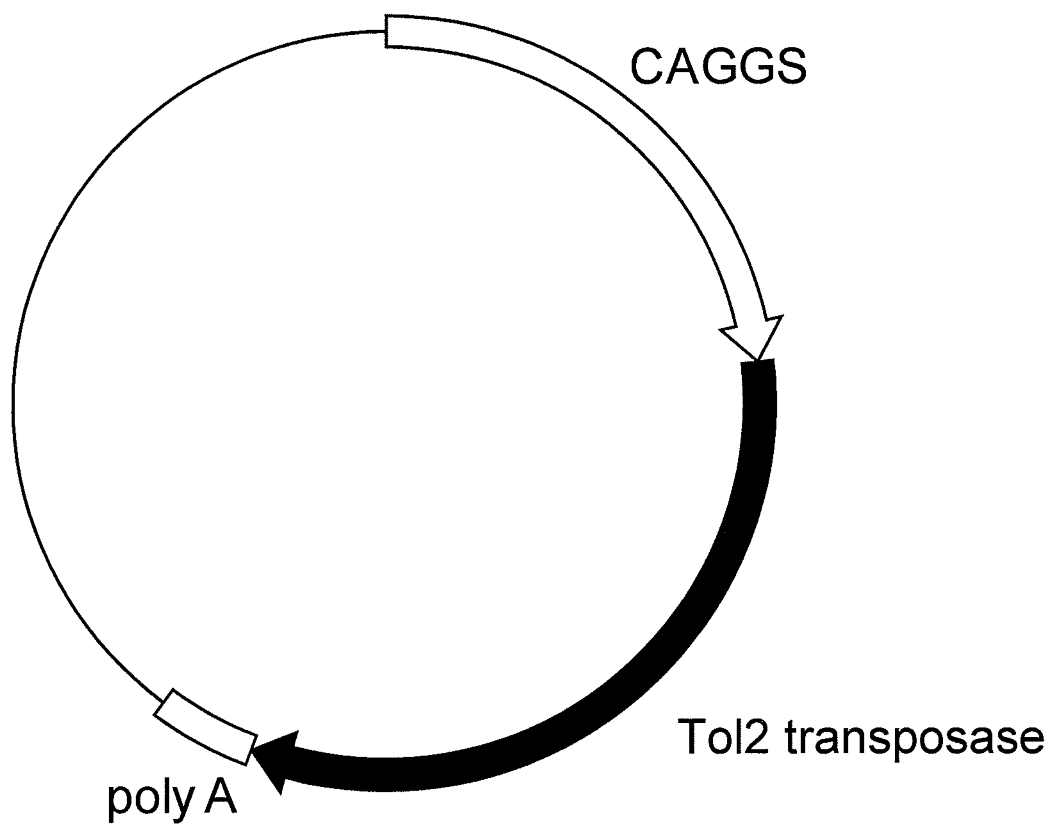
FIG. 3 shows a schematic illustration of a Tol2 transposase expression vector. CAGGS represents a CAGGS promoter, poly A represents a polyadenylation site, and TPase cDNA represents a Tol2 transposase cDNA.

The transposase was expressed using an expression vector independent of the expression vector of the antibody of interest. That is, a gene which is encoding a medaka fish-derived Tol2 transposase (SEQ ID NO:4) was inserted into a downstream of the CAGGS promoter of a pCAGGS vector (Gene, 108, 193-200, 1991) and used as the expression vector (FIG. 3).

Example 3

(1) Preparation of Suspension CHO Cell

An adhesive CHO cell which had been cultured using an α-MEM medium (manufactured by Invitrogen) containing 10% serum (FCS) was peeled off and recovered by a trypsin treatment and shaking-cultured at 37° C. in a 5% $CO_2$ incubator using fresh α-MEM medium containing 10% FCS. Several days thereafter, growth of these cells was confirmed and then shaking culture was carried out by seeding them into a α-MEM medium containing 5% FCS at a concentration of $2\times10^5$ cells/ml.

Further several days thereafter, the inoculation was similarly carried out using the α-MEM medium containing 5% FCS. Finally, a cell adapted to the suspension culture was prepared by repeating the sub-culture and shaking culture using serum-free α-MEM medium and confirming that the cells have the same growing ability of the case of their culturing in the presence of serum.

(2) Preparation of Antibody-Producing CHO Cell

The transposon vector for expressing the anti-human influenza M2 antibody prepared in Example 1 and Example 2 (hereinafter referred to as transposon vector) and Tol2 transposase expression vector pCAGGS-T2TP (FIG. 3, Kawakami K. & Noda T., *Genetics,* 166, 895-899 (2004)) were used as the expression vectors. In addition, the anti-human influenza M2 antibody expression vector having no transposon sequences was used as the control.

By introducing the aforementioned expression vectors into the suspension culture-adapted CHO-K1 cell (American Type Culture Collection Cat. No. CCL-61) or HEK293 cell (FreeStyle 293F cell, manufactured by Invitrogen), the frequencies of obtaining cycloheximide-resistant clones were compared.

Each cells ($4\times10^6$ cells) was suspended in 400 μl of PBS, and the transposon vector for expressing the anti-human influenza M2 antibody (10 μg) and Tol2 transposase expression vector (25 μg) were co-transfected directly in the form of circular DNA by electroporation. In this connection, in order to express the Tol2 transposase transiently, the Tol2 transposase expression vector was directly introduced in the form of circular DNA for the purpose of preventing from integrating into the host chromosome.

In addition, as the control, the anti-human influenza M2 antibody expression vector (10 μg) was linearized by a restriction enzyme and then introduced into each cells, in accordance with the standard gene transfer method by electroporation.

The electroporation was carried out using a cuvette of 4 mm in gap width (manufactured by Bio-Rad®), using an electroporator (Gene Pulser Xcell™ System (manufactured by Bio-Rae)) under conditions of 300 V in voltage, 500 μF in electrostatic capacity and room temperature.

After the transfection by electroporation, each cell was seeded into three 96-well plates and cultured in a $CO_2$ incubator for 3 days using the EX-CELL 325-PF medium manufactured by SAFC Biosciences for the CHO cell, and the FreeStyle-293 medium (manufactured by Invitrogen) for the HEK293 cell.

Next, from the day of medium exchange on the 4th day of the transfection, 3 μg/ml of cycloheximide was added to the medium so that the cells were cultured in the presence of cycloheximide, followed by culturing for 3 weeks while carrying out the medium exchange in every week.

After culturing for 3 weeks, the number of wells in which cycloheximide-resistant colonies were found was counted. The results are shown in Table 1 and Table 2.

TABLE 1

Comparison of the numbers of cycloheximide-resistant cells (CHO cell)

| | Transposon vector | Conventional vector |
|---|---|---|
| Test 1 | 155/288 | 0/288 |
| Test 2 | 100/288 | 0/288 |
| Test 3 | 94/288 | 0/288 |

TABLE 2

Comparison of the numbers of cycloheximide-resistant cells (HEK293 cell)

| | Transposon vector | Conventional vector |
|---|---|---|
| Test 1 | 0/288 | 0/288 |
| Test 2 | 0/288 | 0/288 |
| Test 3 | 0/288 | 0/288 |

As shown in Table 1, each the anti-human influenza M2 antibody expression transposon vector or anti-human influenza M2 antibody expression vector was introduced into the suspension CHO-K1 cell. As a result, cycloheximide-resistant transformants were not obtained from the cell introduced with anti-human influenza M2 antibody expression vector like the case of other cell lines, but cycloheximide-resistant transformants were obtained from the cell introduced with transposon vector for expressing anti-human influenza M2 antibody with a high frequency.

On the other hand, as shown in Table 2, cycloheximide-resistant transformants were not obtained when either of the transposon vector for expressing anti-human influenza M2 antibody and anti-human influenza M2 antibody expression vector was introduced into the HEK293 cell.

Based on these results, it was found that the intended protein-encoded gene and cycloheximide resistance gene which were inserted between a pair of transposon sequences are efficiently introduced into the chromosome of the host cell, namely a suspension mammalian cell.

(3) Examination on the Antibody Production by Suspension CHO Cell and Adhesive CHO Cell In order to examine antibody production efficiency by a suspension CHO cell or an adhesive CHO cell, the amounts of antibodies produced by respective cell lines were examined. As the suspension CHO cell, the suspension CHO-K1 cell adapted to suspension culture was used. In addition, as the adhesive CHO cell, the adhesive CHO-K1 cell before adaptation to suspension culture was used.

The anti-human influenza M2 antibody expression transposon vector (10 μg) and Tol2 transposase expression vector (25 μg) were introduced into the suspension CHO-K1 cell and adhesive CHO-K1 cell by means of electroporation, respectively. Thereafter, the suspension CHO-K1 cell and the adhesive CHO-K1 cell were seeded into three 96-well plates for each cell.

A medium for suspension cells (EX-CELL 325-PF, manufactured by SAFC Biosciences) was used for the suspension CHO-K1 cell, and the α-MEM medium containing 10% serum was used for the adhesive CHO-K1 cell. Each cell was cultured in a $CO_2$ incubator for 3 days. From the day of medium exchange on the 4th day of the transfection, 3 μg/ml of cycloheximide was added to the medium so that the cells were cultured in the presence of cycloheximide and the cells were further cultured for 3 weeks. In this case, the medium exchange was carried out every week.

For the suspension CHO-K1 cell, $1\times10^6$ of the cells were seeded into a 6-well plate and shaking-cultured in a $CO_2$ incubator for 3 days, and the amount of the anti-human influenza M2 antibody protein was measured by HPLC using the culture supernatant.

For the adhesive CHO-K1 cell, medium exchange was carried out when the cell reached confluent on a 6-well plate ($2\times10^6$ cells), and 3 days after static culture, the amount of the antibody protein was measured by HPLC using the culture supernatant.

The antibody concentration in the culture supernatant was measured in accordance with the method described in *Yeast Res.*, 7 (2007), 1307-1316. The results are shown in FIG. 4A and FIG. 4B.

Figure 4A:
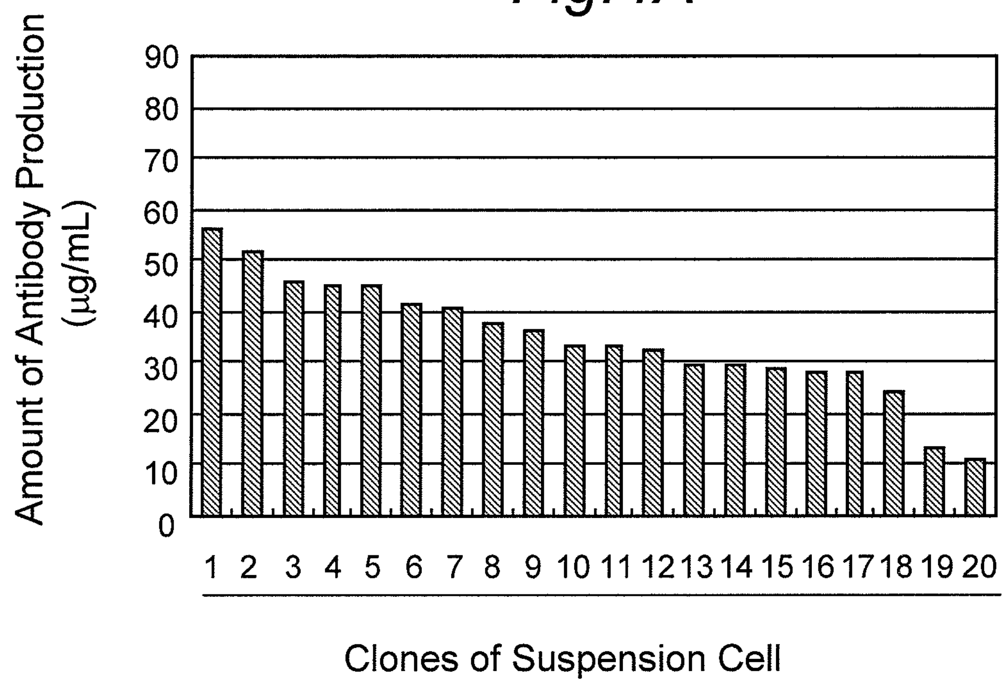
FIG. 4A shows a result of examining expression level of an anti-human influenza M2 antibody in a suspension CHO-K1 cell when a Tol2 transposon vector for expressing an anti-human influenza M2 antibody was used. The ordinate shows the amount of antibody production (μg/ml), and the abscissa shows the number of transgenic clones of the suspension CHO-K1 cell.
Figure 4B:
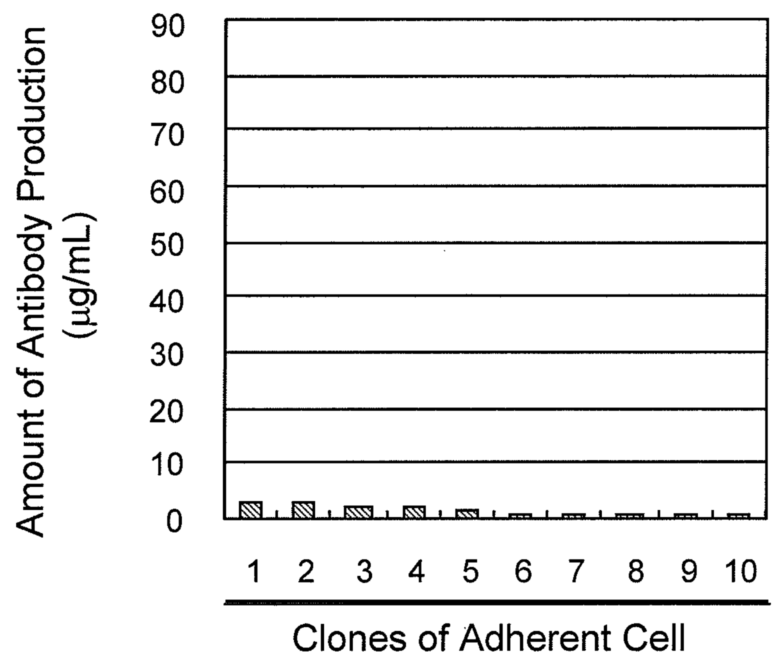
FIG. 4B shows a result of examining expression level of an anti-human influenza M2 antibody in an adhesive CHO-K1 cell when a Tol2 transposon vector for expressing an anti-human influenza M2 antibody was used. The ordinate shows the amount of antibody production (μg/ml), and the abscissa shows the number of transgenic clones of the adhesive CHO-K1 cell.

As shown in FIG. 4A, a large number of cells showing a markedly high antibody expression level were obtained when the CHO-K1 cell adapted to suspension culture was used. On the other hand, as shown in FIG. 4B, only the cells showing an expression level of the HPLC detection limit (5 μg/ml) or less were obtained when the adhesive CHO-K1 cell was used.

Based on these results, it was found that, for the expression of a protein of interest using a transposon vector, the protein of interest can be expressed at a high level when a suspension mammalian cell is used.

In addition, it was found from the results of Examples 1 to 3 that the method of the invention can be used as a novel method for producing a protein of interest, by efficiently preparing a production cell which can highly express an exogeneous gene using a suspension mammalian cell adapted to suspension culture.

Example 4

Preparation of Tol1 Transposon Vector for Expressing Anti-Human Influenza M2 Antibody In the same manner as in Example 1, a plasmid which contains a gene expression cassette for mammalian cells, comprising an arbitrary human antibody gene and a drug resistance marker gene inserted between a pair of Tol1 transposon sequences, was used as a protein expression plasmid vector.

Each DNA of the used genes was chemically synthesized artificially based on the known sequence information or obtained by preparing primers of its both terminal sequences and carrying out PCR using an appropriate DNA source as the template. For the gene manipulation to be carried out later, a site cleaved by a restriction enzyme was added to the end of the primer.

Among the non-autonomous Tol1 transposon nucleotide sequence shown in SEQ ID NO:13 of Sequence Listing (WO2008/072540), the nucleotide sequence at positions 1 to 200 (Tol1-L sequence) (SEQ ID NO:14) and the nucleotide sequence at positions 1351 to 1855 (Tol1-R sequence) (SEQ ID NO:15) were used as the transposon sequences.

Each of the synthetic DNA fragments comprising each a pair of transposon sequences was prepared by the following method. A DNA fragment comprising a nucleotide sequence in which a recognition sequence of a restriction enzyme NruI was connected to both of the 5'-terminal and 3'-terminal of the Tol1-R sequence. Then, a DNA fragment comprising a nucleotide sequence in which a recognition sequence of a restriction enzyme FseI was connected to the 5'-terminal of the Tol1-L sequence and a restriction enzyme AscI was connected to the 3'-terminal thereof.

Next, the thus prepared DNA fragments comprising Tol1-R sequence and Tol1-L sequence were inserted into the expression vector N5LG1-M2-Z3 vector. The DNA fragment comprising the Tol1-R sequence was inserted into the restriction enzyme NruI site of the N5LG1-M2-Z3 vector, existing on the 5'-terminal side of a gene fragment comprising the antibody gene expression cassette and a resistance marker gene, and the DNA fragment comprising the Tol1-L sequence was inserted into the restriction enzyme FseI and AscI sites existing on the 3'-terminal side.

Figure 5:
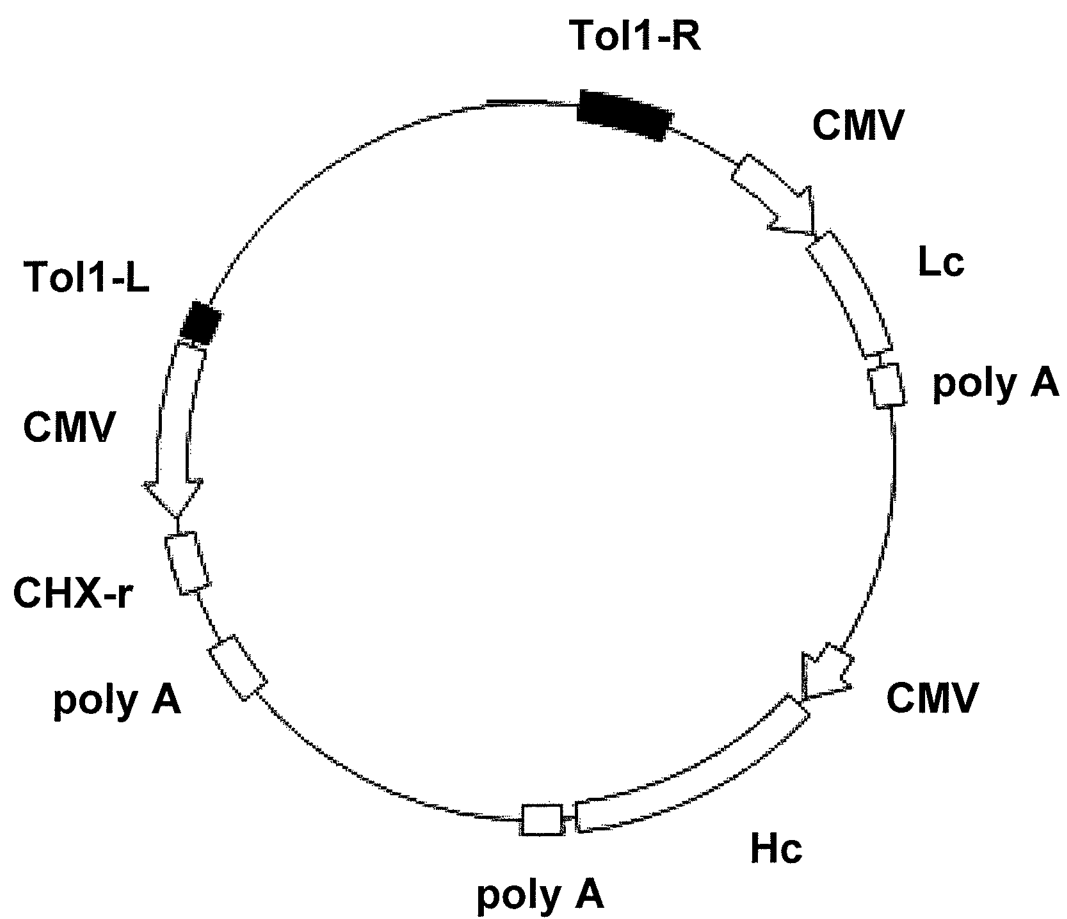
FIG. 5 shows a schematic illustration of a Tol1 transposon vector for expressing an anti-human influenza M2 antibody. Tol1-L represents a left end Tol1 transposon (SEQ ID NO:14), Tol1-R represents a right end Tol1 transposon (SEQ ID NO:15), CMV represents a CMV promoter, poly A represents a polyadenylation site, Hc represents a human antibody H chain cDNA, Lc represents a human antibody L chain cDNA, and CHX-r represents a cycloheximide resistance gene.

In addition, Tol1 transposon vector for expressing an anti-human influenza M2 antibody was constructed (FIG. 5) by inserting a cycloheximide resistance gene expression cassette connected with a resistance gene for cycloheximide (a gene in which proline at position 54 in the human ribosomal protein L36a was mutated to glutamine) into the FseI recognition site of the N5LG1-M2-Z3 vector connected with the Tol1 transposon sequence, under the control of the CMV enhancer/promoter.

Example 5

Preparation of Tol1 Transposase Expression Vector

Figure 6:
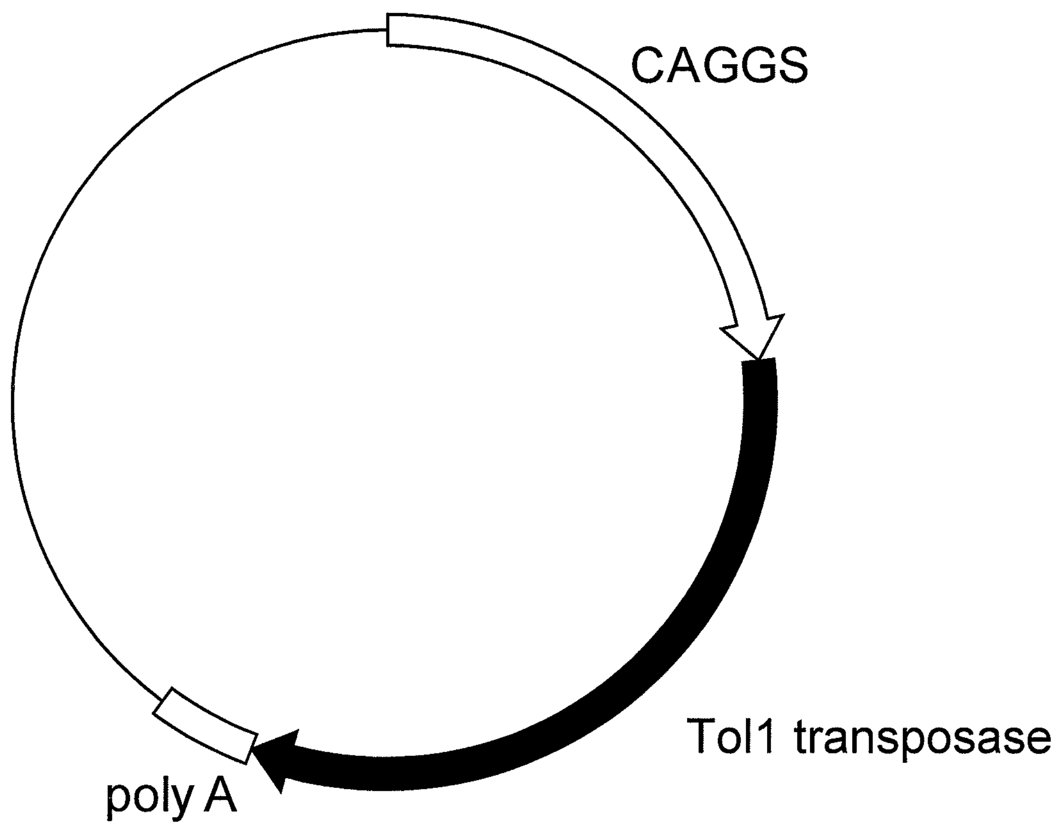
FIG. 6 shows a schematic illustration of a Tol1 transposase expression vector. CAGGS represents a CAGGS promoter, poly A represents a polyadenylation site, and TPase cDNA represents a Tol1 transposase cDNA.

The transposase was expressed using an expression vector independent from the expression vector of the antibody of interest. That is, a Tol1 transposase gene expression cassette connected with a DNA fragment encoding a medaka fish-derived Tol1 transposase, containing the nucleotide sequence shown in SEQ ID NO:16 of Sequence Listing, was inserted into pBluescriptII SK (+) (manufactured by Stratagene) under the CMV enhancer/promoter control and used as the expression vector pTol1ase (FIG. 6).

Example 6

(1) Preparation of Antibody-Producing CHO Cell

The Tol1 transposon vector for expressing the anti-human influenza M2 antibody (hereinafter referred to as Tol1 transposon vector) and Tol1 transposase expression vector pTol1ase of Example 4 and Example 5 were used as the expression vectors. In addition, the CHO-K1 cell prepared by adapting to suspension culture in the same manner as in Example 3(1) was used as the cell.

The aforementioned expression vectors were introduced into the CHO-K1 cell adapted to suspension culture, and the frequency of obtaining clones resistant to cycloheximide was measured. The CHO-K1 cell adapted to suspension culture ($4\times10^6$ cells) were suspended in 400 μl of PBS, and the Tol1 transposon vector for expressing the anti-human influenza M2 antibody (10 μg) and Tol1 transposase expression vector (50 μg) were co-transfected directly in the form of circular DNA by electroporation. In order to effect transient expression of the Tol1 transposase, the Tol1 transposase expression vector was directly introduced in the form of circular DNA for the purpose of preventing from integrating into the host chromosome.

The electroporation was carried out using a cuvette of 4 mm in gap width (manufactured by Bio-Rad®), using an electroporator (Gene Pulser Xcell™ System (manufactured by Bio-Rae)) under conditions of 300 V in voltage, 500 μF in electrostatic capacity and room temperature.

After the transfection by electroporation, each cell was seeded into two 96-well plates and cultured in a $CO_2$ incubator for 3 days using the EX-CELL 325-PF medium (manufactured by SAFC Biosciences) for the CHO cell. Next, from the day of medium exchange on the 4th day of the transfection, 3 μg/ml of cycloheximide was added to the medium so that the cells were cultured in the presence of cycloheximide, followed by culturing for 3 weeks while carrying out the medium exchange every week.

After the culturing for 3 weeks, the number of wells in which cycloheximide-resistant colonies were found was counted. The results are shown in Table 3. Each of the tests 1 to 3 in Table 3 shows a result of carrying out the gene transfer three times.

TABLE 3

| | Tol1 transposon vector |
|---|---|
| Tests 1 | 133/192 |
| Tests 2 | 67/192 |
| Tests 3 | 122/192 |

As shown in Table 3, when the Tol1 transposon vector for expressing the anti-human influenza M2 antibody was introduced into the suspension CHO-K1 cell, cycloheximide-resistant transformants were obtained at a high frequency similarly to Example 3 in which the Tol2 transposon vector for expressing the anti-human influenza M2 antibody was introduced.

It was found based on these results that the antibody gene and cycloheximide resistance gene inserted between a pair of transposon sequences are efficiently transduced into the chromosome of the host cell, namely the suspension mammalian cell, in the case of using the Tol1 transposon, too.

(2) Examination on Antibody Production by Suspension CHO-K1 Cell

Antibody production efficiency of the suspension CHO-K1 cell was examined using the suspension CHO-K1 cell. The transposon vector for expressing the anti-human influenza M2 antibody (10 μg) and Tol1 transposase expression vector (50 μg) were introduced by electroporation into the suspension CHO-K1 cell adapted to suspension culture.

Thereafter, the cells were seeded into respective two 96-well plates and cultured for 3 days in a $CO_2$ incubator using the suspension culture medium EX-CELL 325-PF. From the medium exchange on the 4th days after the electroporation, the cells were cultured for 3 weeks in the presence of 3 μg/ml of cycloheximide. In this case, the medium exchange was carried out every week.

For the suspension CHO-K1 cell, $1\times10^6$ of the cells were seeded into a 6-well plate and shaking-cultured in a $CO_2$ incubator for 3 days, and amount of the anti-human influenza M2 antibody protein was measured by HPLC using the culture supernatant.

The antibody concentration in culture supernatant was measured in accordance with the method described in *Yeast Res.,* 7 (2007), 1307-1316. The results are shown in FIG. 7.

Figure 7:
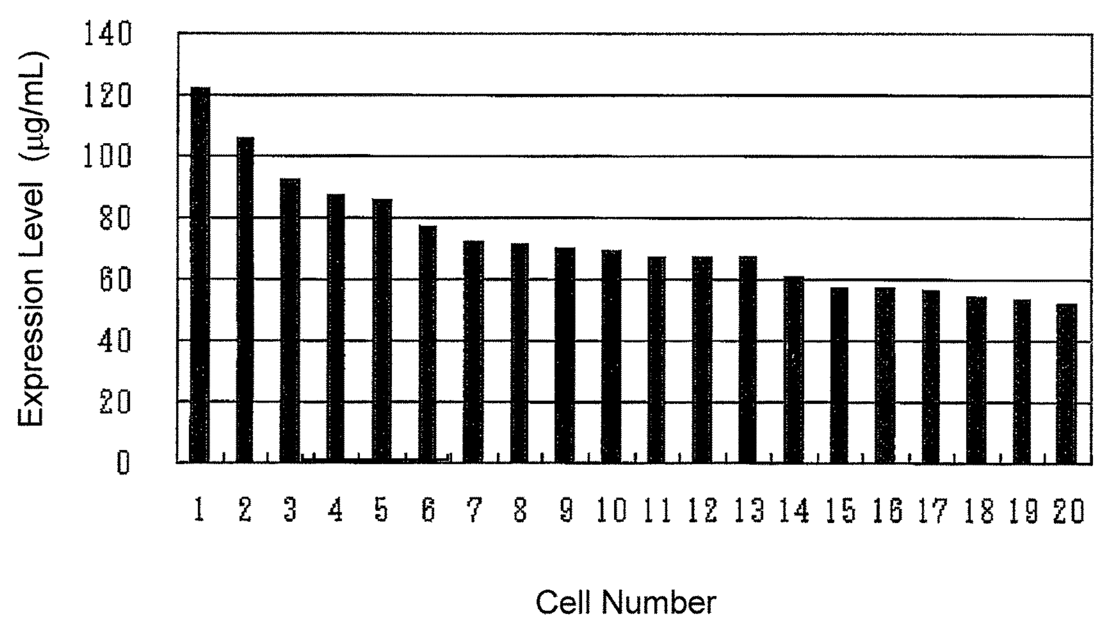
FIG. 7 shows a result of examining expression level of an anti-human influenza M2 antibody in a suspension CHO-K1 cell when a Tol1 transposon vector for expressing an anti-human influenza M2 antibody was used. The ordinate shows the amount of antibody production (μg/ml), and the abscissa shows the number of transgenic clones of the suspension CHO-K1 cell.

As shown in FIG. 7, a large number of cells showing a markedly high antibody expression level were obtained in the case of the use of the Tol1 transposon, too. From this result, it was found that similar to the case of the use of the Tol2 transposon-derived nucleotide sequence, a suspension mammalian cell capable of highly expressing the protein of interest can also be obtained when a Tol1 transposon-derived nucleotide sequence is used as the transposon sequence.

While the invention has been described in detail and with reference to specific embodiments thereof, it will be apparent to one skill in the art that various changes and modifications can be made therein without departing from the spirit and scope thereof.

This application is based on Japanese application No. 2009-140626, filed on Jun. 11, 2009, and U.S. provisional application No. 61/186,138, filed on Jun. 11, 2009, the entire contents of which are incorporated hereinto by reference. All references cited herein are incorporated in their entirety.

What is claimed is:

1. A method selected from the group consisting of (I) and (II):

(I) a method for increasing expression of a protein of interest, comprising introducing an expression vector which comprises a gene fragment comprising a DNA encoding the protein and a selectable marker gene, and transposon sequences at both terminals of the gene fragment, into a suspension mammalian cell; integrating the gene fragment inserted between a pair of the transposon sequences, into a chromosome of the mammalian cell to obtain a mammalian cell capable of expressing the protein; and suspension-culturing the mammalian cell; or (II) a method for increasing expression of a protein of interest, which comprises the following steps (A) to (C):

(A) a step of simultaneously introducing the following expression vectors (a) and (b) into a suspension mammalian cell, (a) an expression vector which comprises a gene fragment comprising a DNA encoding the protein, and transposon sequences at both terminals of the gene fragment, (b) an expression vector which comprises a DNA encoding a transposase which recognizes the transposon sequences and has activity of transferring a gene fragment inserted between a pair of the transposon sequences into a chromosome, (B) a step of transiently expressing the transposase from the expression vector introduced in the step (A) to integrate the gene fragment inserted between a pair of the transposon sequences into a chromosome of the mammalian cell, to obtain a suspension mammalian cell capable of expressing the protein, and (C) a step of suspension-culturing the suspension mammalian cell capable of expressing the protein obtained in step (B);

wherein in the methods of (I) or (II), the pair of transposon sequences are nucleotide sequences derived from a pair of Tol1 transposons or nucleotide sequences derived from a pair of Tol2 transposons, and wherein the suspension mammalian cell is at least one selected from a suspension CHO cell in which a CHO cell is adapted to suspension culture, a PER.C6 cell, a rat myeloma cell YB2/3HL.P2.G11.16Ag.20 (or YB2/0) and a suspension mouse myeloma cell NS0 adapted to suspension culture.

2. The method according to claim 1, (I) wherein the suspension mammalian cell is a cell capable of surviving and proliferating in a serum-free medium;

(II) wherein the selectable marker gene is a cycloheximide resistance gene; and/or (III) wherein the pair of transposon sequences are nucleotide sequences derived from a pair of DNA-type transposons which function in a mammalian cell.

3. The method according to claim 1, wherein the CHO cell is at least one selected from CHO-K1, CHO-K1SV, DUKXB11, CHO/DG44, Pro-3 and CHO-S.

4. The method according to claim 2, wherein the cycloheximide resistance gene is a gene encoding a mutant of human ribosomal protein L36a.

5. The method according to claim 4, wherein the mutant is a mutant in which proline at position 54 of the human ribosomal protein L36a is substituted with other amino acid.

6. The method according to claim 5, wherein the other amino acid is glutamine.

7. The method according to claim 1, (I) wherein the nucleotide sequences derived from a pair of Tol2 transposons are a nucleotide sequence comprising the nucleotide sequence shown in SEQ ID NO:2 and the nucleotide sequence shown in SEQ ID NO:3; or (II) wherein the nucleotide sequences derived from a pair of Tol1 transposons are the nucleotide sequence shown in SEQ ID NO:14 and the nucleotide sequence shown in SEQ ID NO:15.

8. A suspension mammalian cell capable of increasing expression of a protein of interest, (I) into which an expression vector comprising a gene fragment comprising a DNA encoding the protein and a selectable marker gene, and transposon sequences at both terminals of the gene fragment is introduced, to integrate the gene fragment inserted between a pair of the transposon sequences into a chromosome; or (II) into which an expression vector (a) comprising a gene fragment comprising a DNA encoding the protein and a selectable marker gene, and transposon sequences at both terminals of the gene fragment, and an expression vector (b) comprising a DNA encoding a transposase which recognizes the transposon sequences and has activity of transferring the gene fragment inserted between a pair of the transposon sequences into a chromosome to integrate the gene fragment inserted between a pair of the transposon sequences into the chromosome, wherein in the methods of (I) or (II), the pair of transposon sequences are nucleotide sequences derived from a pair of Tol1 transposons or nucleotide sequences derived from a pair of Tol2 transposons, and wherein the suspension mammalian cell is at least one selected from a suspension CHO cell in which a CHO cell is adapted to suspension culture, a PER.C6 cell, a rat myeloma cell YB2/3HL.P2.G11.16Ag.20 (or YB2/0) and a suspension mouse myeloma cell NS0 adapted to suspension culture.

9. The cell according to claim 8, (I) wherein the cell is a cell capable of surviving and proliferating in a serum-free medium;

(II) wherein the selectable marker gene is a cycloheximide resistance gene; and/or (III) wherein the pair of transposon sequences are nucleotide sequences derived from a pair of DNA type transposons which function in a mammalian cell.

10. The cell according to claim 9, wherein the CHO cell is at least one selected from CHO-K1, CHO-K1SV, DUKXB11, CHO/DG44, Pro-3 and CHO-S.

11. The cell according to claim 9, wherein the cycloheximide resistance gene is a gene encoding a mutant of human ribosomal protein L36a.

12. The cell according to claim 11, wherein the mutant is a mutant in which proline at position 54 of the human ribosomal protein L36a is substituted with other amino acid.

13. The cell according to claim 12, wherein the other amino acid is glutamine.

14. The cell according to claim 8, (I) wherein the nucleotide sequences derived from a pair of Tol2 transposons are the nucleotide sequence shown in SEQ ID NO:2 and the nucleotide sequence shown in SEQ ID NO:3; or (II) wherein the nucleotide sequences derived from a pair of Tol1 transposons are the nucleotide sequence shown in SEQ ID NO:14 and the nucleotide sequence shown in SEQ ID NO:15.

15. The expression vector for increasing expression of a protein of interest according to claim 1 or 8, comprising a gene fragment comprising a DNA encoding a protein of interest and a selectable marker gene, and a pair of transposon sequences at both terminals of the gene fragment; and wherein the pair of transposon sequences are nucleotide sequences derived from a pair of Tol1 transposons or nucleotide sequences derived from a pair of Tol2 transposons.

16. The expression vector according to claim 15, (I) wherein the nucleotide sequences derived from a pair of the Tol2 transposons are the nucleotide sequence shown in SEQ ID NO:2 and the nucleotide sequence shown in SEQ ID NO:3; or (II) wherein the nucleotide sequences derived from a pair of the Tol1 transposons are the nucleotide sequence shown in SEQ ID NO:14 and the nucleotide sequence shown in SEQ ID NO:15.

* * * * *